US011490910B2

(12) United States Patent
Leuthardt et al.

(10) Patent No.: US 11,490,910 B2
(45) Date of Patent: Nov. 8, 2022

(54) BALLOON ENCAPSULATION AND ISOVOLUMETRIC SUCTION THROMBECTOMY CATHETER AND METHODS THEREOF

(71) Applicant: Washington University, St. Louis, MO (US)

(72) Inventors: Eric Leuthardt, St. Louis, MO (US); Mohamed Zayed, St. Louis, MO (US); Guy Genin, St. Louis, MO (US); Joshua Osbun, St. Louis, MO (US); Gayan De Silva, St. Louis, MO (US); Sanghun A. Lee, St. Louis, MO (US); Dillon Williams, St. Louis, MO (US); Alexander Wirtz, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/467,926

(22) Filed: Sep. 7, 2021

(65) Prior Publication Data

US 2022/0000498 A1    Jan. 6, 2022

Related U.S. Application Data

(63) Continuation of application No. 17/280,222, filed as application No. PCT/US2019/053294 on Sep. 26, 2019.
(Continued)

(51) Int. Cl.
*A61B 17/22*    (2006.01)
*A61M 25/00*    (2006.01)
(Continued)

(52) U.S. Cl.
CPC ...... *A61B 17/22* (2013.01); *A61B 17/320725* (2013.01); *A61M 25/003* (2013.01);
(Continued)

(58) Field of Classification Search
CPC ............ A61B 17/22; A61B 17/320725; A61B 2017/22051; A61B 2017/22054;
(Continued)

(56) References Cited

U.S. PATENT DOCUMENTS 5,059,178 A     10/1991   Ya
5,279,546 A *   1/1994    Mische ............ A61B 17/22012
                                                    604/101.03
(Continued)

FOREIGN PATENT DOCUMENTS

WO          2020069216 A1    4/2020

OTHER PUBLICATIONS

International Search Report and Written Opinion dated Dec. 13, 2019 from related International Patent Application No. PCT/US2019/53294; 9 pgs.

*Primary Examiner* — Tuan V Nguyen
(74) *Attorney, Agent, or Firm* — Polsinelli, PC

(57) ABSTRACT

The disclosure provides for an adjustable catheter system with isovolumetric suction and restoration of fluid for the removal of a thrombus and a method of use thereof. The catheter system includes an inner catheter and an outer sheath surrounding at least a portion of the inner catheter. The inner catheter may include at least three lumina extending from the proximal end to the distal end of the inner catheter, at least one infusion fenestration along the infusion segment, and a distal encapsulation balloon at the distal end. The outer sheath may include at least three lumina extending from the proximal end to the distal end of the outer sheath and a proximal encapsulation balloon at the distal end. The
(Continued)

catheter system may further include an agitator for mechanical morcellation of the thrombus.

23 Claims, 27 Drawing Sheets

Related U.S. Application Data

(60) Provisional application No. 62/842,975, filed on May 3, 2019, provisional application No. 62/736,890, filed on Sep. 26, 2018.

(51) Int. Cl.
| | |
|---|---|
| *A61B 17/3207* | (2006.01) |
| *A61M 25/06* | (2006.01) |
| *A61M 25/10* | (2013.01) |
| *A61B 17/32* | (2006.01) |

(52) U.S. Cl.
CPC .... *A61M 25/0026* (2013.01); *A61M 25/0043* (2013.01); *A61M 25/0662* (2013.01); *A61M 25/1011* (2013.01); *A61B 2017/22054* (2013.01); *A61B 2017/22062* (2013.01); *A61B 2017/22079* (2013.01); *A61B 2017/22082* (2013.01); *A61B 2017/320012* (2013.01); *A61M 2025/0004* (2013.01); *A61M 2025/0057* (2013.01); *A61M 2025/0681* (2013.01); *A61M 2025/109* (2013.01); *A61M 2025/1052* (2013.01); *A61M 2025/1061* (2013.01)

(58) Field of Classification Search
CPC  A61B 2017/22079; A61B 2017/22084; A61B 2017/22062; A61B 2017/22082; A61B 2017/32012

See application file for complete search history.

(56) References Cited

U.S. PATENT DOCUMENTS

| | | |
|---|---|---|
| 5,460,610 A | 10/1995 | Michael et al. |
| 5,462,529 A | 10/1995 | Simpson et al. |
| 5,865,801 A | 2/1999 | Houser |
| 6,030,397 A | 2/2000 | Monetti et al. |
| 6,126,635 A | 10/2000 | Simpson et al. |
| 6,338,709 B1 * | 1/2002 | Geoffrion ............ A61N 5/1002 600/3 |
| 6,398,773 B1 | 6/2002 | Bagaoisan et al. |
| 6,485,500 B1 | 11/2002 | Kokish et al. |
| 6,575,932 B1 * | 6/2003 | O'Brien .............. A61M 25/007 604/101.01 |
| 2002/0016565 A1 | 2/2002 | Zadno-Azizi et al. |
| 2013/0178790 A1 | 7/2013 | Tekulve |

* cited by examiner

BALLOON ENCAPSULATION AND ISOVOLUMETRIC SUCTION THROMBECTOMY CATHETER AND METHODS THEREOF

CROSS REFERENCE TO RELATED APPLICATIONS

This application is a continuation application of U.S. application Ser. No. 17/280,222, filed Mar. 26, 2021 which claims the benefit of International Patent Application No. PCT/US2019/053294, filed Sep. 26, 2019, which claims priority to U.S. Provisional Application No. 62/842,975, filed May 3, 2019, and U.S. Provisional Application No. 62/736,890, filed Sep. 26, 2018, the contents of which are entirely incorporated by reference herein.

GOVERNMENTAL RIGHTS

This invention was made with government support under CMMI1548571 awarded by the National Science Foundation. The government has certain rights in the invention.

FIELD

The present disclosure is directed to a balloon encapsulation suction thrombectomy catheter and methods of use thereof.

BACKGROUND

Over the past two decades the incidence and prevalence of deep vein thrombosis (DVTs) and pulmonary embolism (PE) have increased due to higher use of indwelling central venous catheters (CVCs), inferior vena cava (IVC) filters, and venous stent implantations. The most common risk factors for DVT and/or PE include age, obesity, pregnancy, pharmacological contraception, malignant disease, and immobility. The etiological factors of DVTs and PEs are found among Virchow's triad of venous blood stasis, venous injury, and hypercoagulability. Under these circumstances, foci of thrombus can develop and propagate to points of decreased venous outflow, i.e. behind valves or at venous branch points, and lead to an organized column of acute thrombus. Incomplete resolution can lead to further thrombus propagation, instability, fragmentation, chronic thromboembolic pulmonary hypertension (CTEPH), and venous thromboembolism (VTE). However, even when thrombus is stabilized and propagation is prevented, the resultant residual obstructive chronic DVT within the venous structure can lead to post-thrombotic syndrome (PTS).

The 2016 American College of Chest Physicians (ACCP) recommends for patients with acute DVT initial treatment with low-molecular weight heparin (LMWH) followed by a course of therapeutic anticoagulation (AC), but it does not produce clot lysis and prevent PTS. Catheter-based endovascular technology such as catheter-directed thrombolysis (CDT), rheolytic pharmacomechanical thrombectomy, and mechanical suction thrombectomy each have their advantages and disadvantages for the treatment of VTE. However, all have limited efficacy in the treatment of PE.

There are currently no endovascular devices that are specifically designed for the treatment of massive (PE causing hemodynamic compromise) and sub-massive PEs (PE causing cardiac dysfunction). Additionally, recent evidence from various large multicenter randomized controlled trials has questioned the efficacy of CDT endovascular devices. CDT endovascular devices have been shown to reduce PTS, but ultimately did not alter quality of life for patients with proximal DVT. In particular, existing technologies have the following limitations: lack of a clot removal device tailored for the iliocaval venous system, ineffective localized thrombolysis leading to systemic dispersal, ineffective encapsulation of clot during lysis to avoid VTE, and atraumatic thrombectomy to avoid venous wall damage and long-term PTS.

Accordingly, there remains a need for a feasible and translatable treatment strategy for DVT and massive and sub-massive PEs that minimizes the risk of VTE and PTS to reduce the high morbidity associated with this condition.

BRIEF SUMMARY

The disclosure provides for a catheter system for the removal of a thrombus. In some embodiments, the catheter system may be used for the treatment of PE. In an aspect, the catheter system may include an inner catheter having a proximal end, an infusion segment, and a distal end. The inner catheter may include at least one infusion fenestration along the infusion segment and a distal encapsulation balloon at the distal end. The catheter system may also include an outer sheath having a proximal end and a distal end. The outer sheath may include a proximal encapsulation balloon at the distal end. The outer sheath surrounds at least a portion of the inner catheter. In some aspects, the catheter system further includes an agitator operable to agitate the thrombus.

In an aspect, the inner catheter further includes at least three lumina extending from the proximal end to the distal end of the inner catheter, for example, an inflation lumen, a guide wire lumen, and an infusion lumen. In an aspect, the infusion segment comprises more than one infusion fenestration fluidly connected to the infusion lumen.

In another aspect, the outer sheath may further include at least three lumina extending from the proximal end to the distal end of the outer sheath, for example, an inflation lumen, a suction lumen, and a catheter lumen. The inner catheter may be positioned within the catheter lumen.

In an aspect, the agitator includes a plurality of protrusions. The agitator may advance and retract over the catheter lumen. In another aspect, the agitator may be a rotatable wire that extends from the distal end of the outer sheath. The distal encapsulation balloon and the proximal may form a treatment area. The thrombus to be removed may be contained within the treatment area. The infusion segment is within the treatment area. In an aspect, the inner catheter further comprises a manifold at its proximal end comprising an infusion port, a balloon inflation port, and a guidewire access port, wherein each port is fluidly connected to one of the at least there lumina of the inner catheter. In another aspect, the outer sheath further comprises a manifold at its proximal end comprising a suction port, a balloon inflation port, and a device access port, wherein each port is fluidly connected to one of the at least there lumina of the outer sheath.

Further provided herein is a method of removing a thrombus in a patient in need thereof. In an aspect, the method may include inserting the catheter system of claim 1 to a treatment area, inflating the distal encapsulation balloon through an inflation lumen of the inner catheter, inflating the proximal encapsulation balloon through an inflation lumen of the outer sheath, mechanically lysing the thrombus with the agitator, infusing an infusion solution to the treatment area through the at least one infusion fenestration, applying negative suction to the treatment area through a suction lumen of the outer sheath, and removing the catheter system from the patient.

In an aspect, the infusion solution is a thrombolytic solution, saline, or combinations thereof. The thrombolytic solution may include tPA. In an aspect, the negative suction may be applied for about 2 minutes. In another aspect, mechanically lysing the thrombus comprises advancing and retracting the agitator over the catheter lumen. In yet another aspect, mechanically lysing the thrombus may include rotating the agitator. In an aspect, greater than about 90% luminal patency of the treatment area is restored.

Also provided herein is a method of treating a pulmonary embolism in a patient in need thereof, the method comprising advancing the catheter system from a femoral vein cannulation or an internal jugular vein cannulation.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as various embodiments of the disclosure and should not be construed as a complete recitation of the scope of the disclosure, wherein.

DETAILED DESCRIPTION

Figure 1:
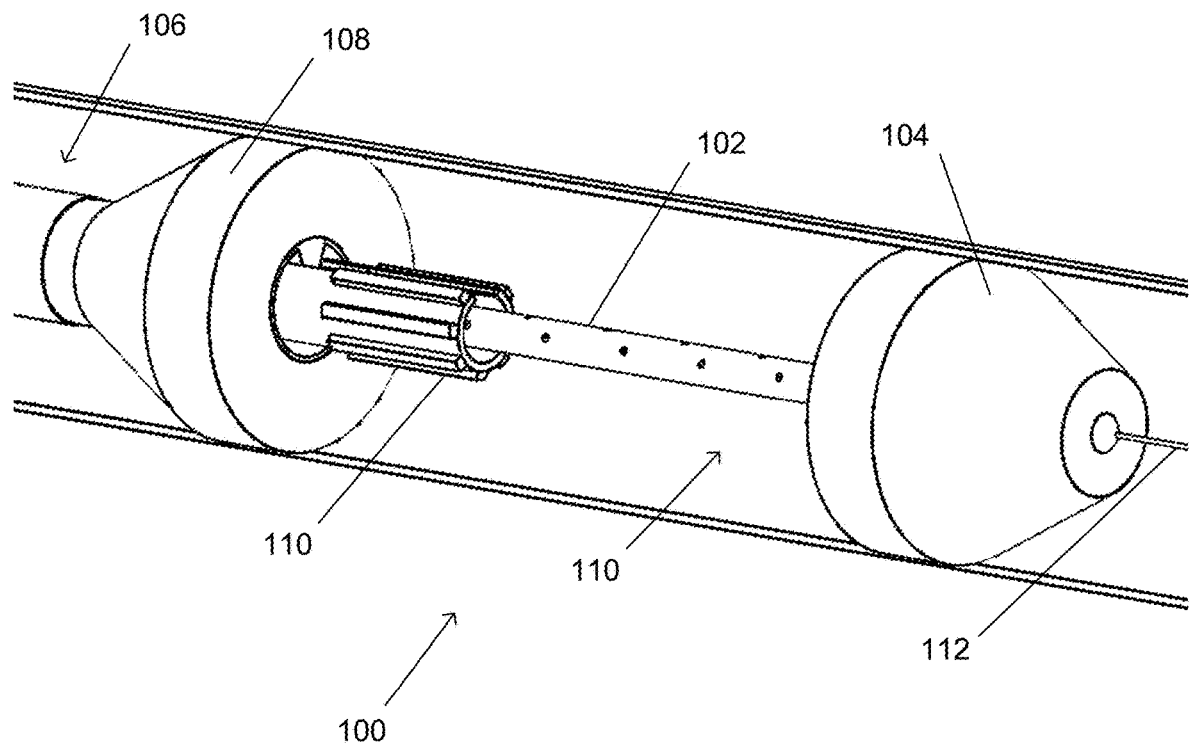
FIG. 1 is a perspective view of the catheter system within a vessel relative to an intraluminal guide wire in one embodiment.

The disclosure may be understood by reference to the following detailed description, taken in conjunction with the drawings as described below. It is noted that, for purposes of illustrative clarity, certain elements in various drawings may not be drawn to scale.

CDT and PCDT have ineffective localized thrombolysis, leading to systemic bleeding side effects. Another major limitation of CDT and PCDT compared to AC alone is the 1.5-fold increase risk of PE and 2-fold increased need for an adjunct IVC filter placement to avoid thrombus embolization during treatment. Therefore, CDT and PCDT have ineffective encapsulation of the treatment zone to avoid dangerous thromboembolization during procedures. Mechanical suction thrombectomy aims to reduce the risk of PE. However, current suction thrombectomy devices have non-suitable calibers and lack proven efficacy for treatment of DVT. The balloon encapsulation and isovolumetric suction thrombectomy catheter provided herein overcomes all the major gaps in the current endovascular thrombectomy devices for the treatment of 'large-volume' ilio-caval DVT and massive and sub-massive PEs. Therefore, the balloon encapsulation suction thrombectomy catheter may be used for the efficient removal of venous clots from the pulmonary artery, vena cava, and iliac veins.

Disclosed herein are balloon encapsulation suction thrombectomy catheter systems and methods for treatment of massive and sub-massive PEs, IVC and iliac vein DVT. In an embodiment, catheter system provides a minimally invasive solution for efficient and complete removal of a 'large-volume' thrombus from pulmonary arteries. The catheter system may include chemical, mechanical, and/or suction features for maximal thrombectomy efficiency. In an embodiment, the catheter system may be less invasive than existing procedures and devices. For example, a 10-20Fr catheter system, delivered percutaneously, with isovolumeteric infusion and thrombus suction may provide for less invasive manipulation of pulmonary arteries. The catheter system may reduce the operative risk to the patient by maintaining vessel integrity.

In an embodiment, the catheter system may have proximal and distal balloons for encapsulation of a thrombus in a treatment area. In some examples, the proximal and distal thrombus balloons encapsulation of the thrombus may reduce or prevent distal embolization. The distance between the proximal and distal balloons may be adjustable, thus forming an adjustable treatment area that can be used to accommodate a wide range of venous treatment lengths. In another embodiment, the catheter system may perform localized isovolumetric suction thrombectomy. The catheter system may provide localized catheter-directed thrombolysis in the treatment zone, which may reduce the risk of bleeding. The catheter system may also provide localized mechanical thrombolysis using an agitator. In yet another embodiment, the catheter system may provide mechanical agitation of the thrombus with an agitator to facilitate removal through the isovolumetric suction and restoration of fluid in the treatment area.

In an embodiment, the agitator and suction features of the catheter system may facilitate complete thrombectomy. In some embodiments, the catheter system may facilitate at least 90%, at least 95%, at least 98%, at least 99%, or at least 100% thrombus removal.

In an embodiment, the catheter system may minimize the length and uncertainty of surgery time. In some embodiments, the length of surgery using the catheter system may be up to 30 minutes, up to 45 minutes, up to 1 hour, or up to 2 hours. In various embodiments, the catheter system may be used in multiple vessels throughout the body, including, but not limited to the pulmonary artery, vena cava, iliac veins, femoral vein, right atrium, jugular vein, and/or popliteal vein.

Catheter System

In some examples, the catheter system includes an inner catheter, an outer sheath, and/or an agitator. The inner catheter has a proximal end, an infusion segment, and a distal end. The inner catheter further has at least one infusion fenestration along the infusion segment and a distal encapsulation balloon at the distal end. The outer sheath has a proximal end and a distal end. The outer sheath further includes a proximal encapsulation balloon at the distal end. In some examples, the outer sheath surrounds at least a portion of the inner catheter and the distal encapsulation balloon and the proximal encapsulation balloon are separated by a distance along the infusion segment.

Figure 2A:
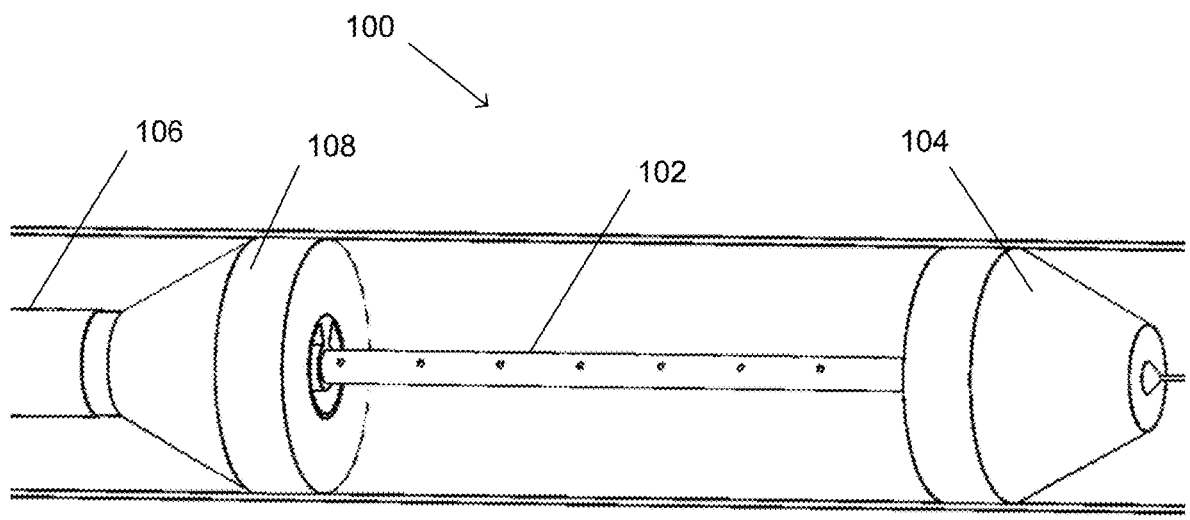
FIG. 2A is a side view of the catheter system deployed intraluminally with the agitator retracted in one embodiment.
Figure 2B:
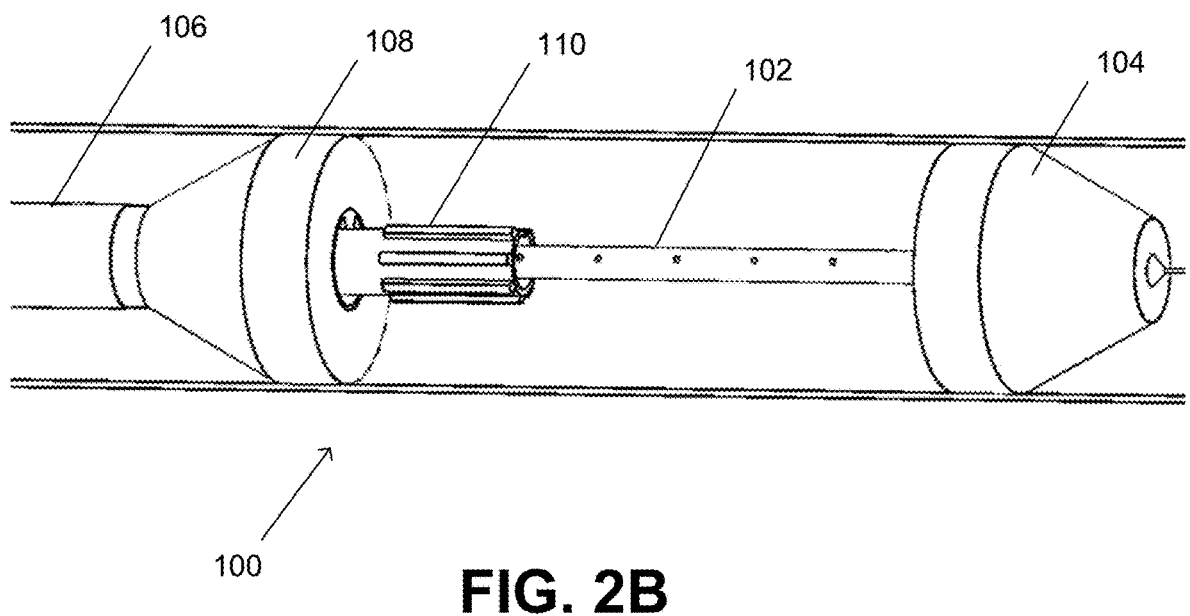
FIG. 2B is a side view of the catheter system deployed intraluminally with the agitator deployed in the treatment area in one embodiment.

FIG. 1 shows the distal end of the catheter system 100 relative to an intraluminal guide wire 112. The catheter system 100 includes an inner catheter 101, a distal balloon 104, an outer sheath 106, a proximal balloon 108, and an agitator 110. FIG. 2A is a side view of the catheter system 100 within a vessel with the proximal balloon 108 and the distal balloon 104 deployed, creating a treatment area with the infusion segment 102, and the agitator retracted within the outer sheath 106. FIG. 2B is a side view of the catheter system 100 within a vessel with the proximal balloon 108 and the distal balloon 104 deployed, creating a treatment area with the infusion segment 102, and the agitator 110 deployed intraluminally.

Figure 3:
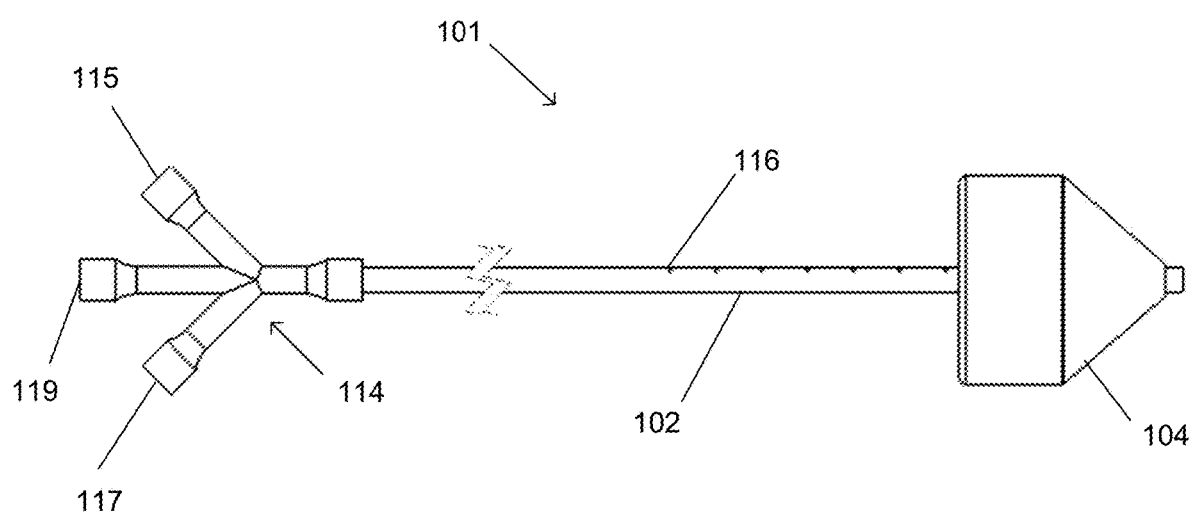
FIG. 3 is side view of the inner catheter that is equipped with an infusion port, balloon inflation port, and guide wire access port in one embodiment. The inner catheter is also composed of an infusion segment with infusion fenestrations and a distal encapsulation balloon.
Figure 4A:
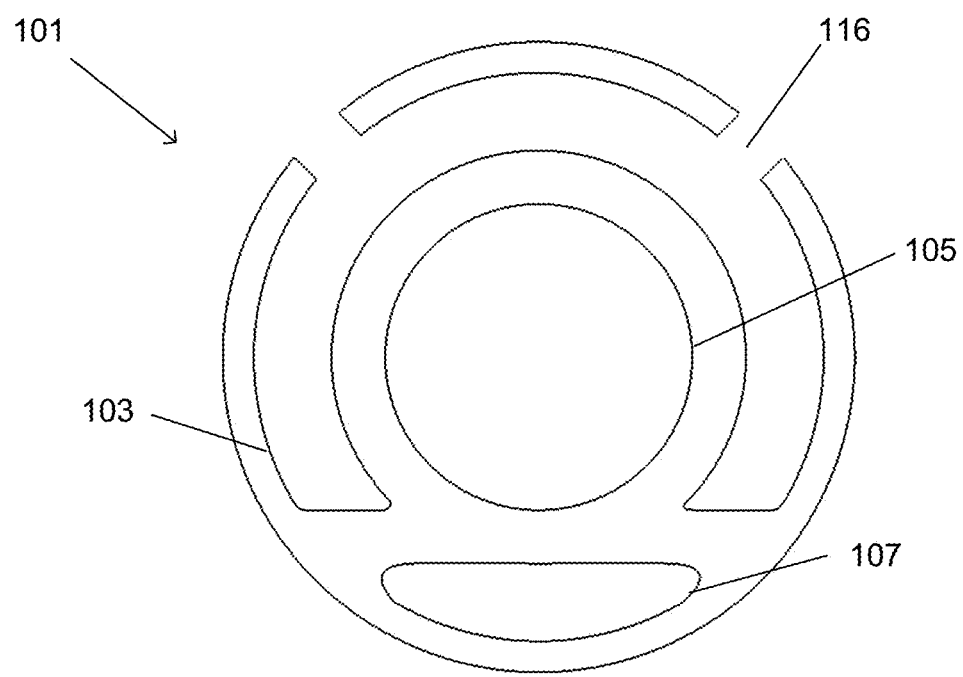
FIG. 4A is a cross-sectional view of the inner catheter multi-lumen design with an infusion lumen, a guide wire lumen, and an inflation lumen in one embodiment.
Figure 4B:
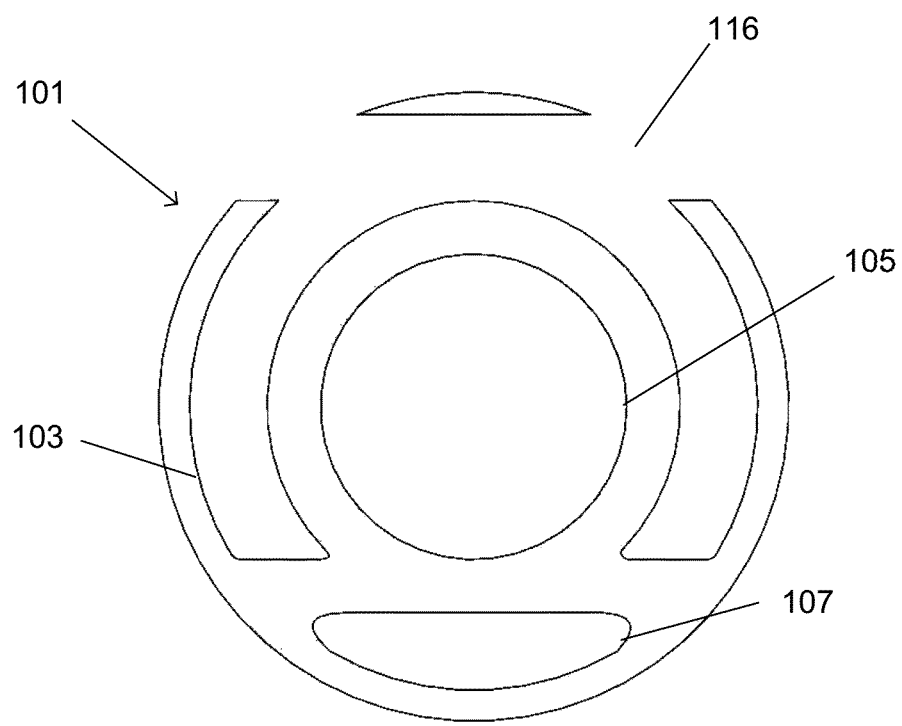
FIG. 4B is a cross-sectional view of the inner catheter multi-lumen design with an infusion lumen, a guide wire lumen, and an inflation lumen in one embodiment.
Figure 4C:
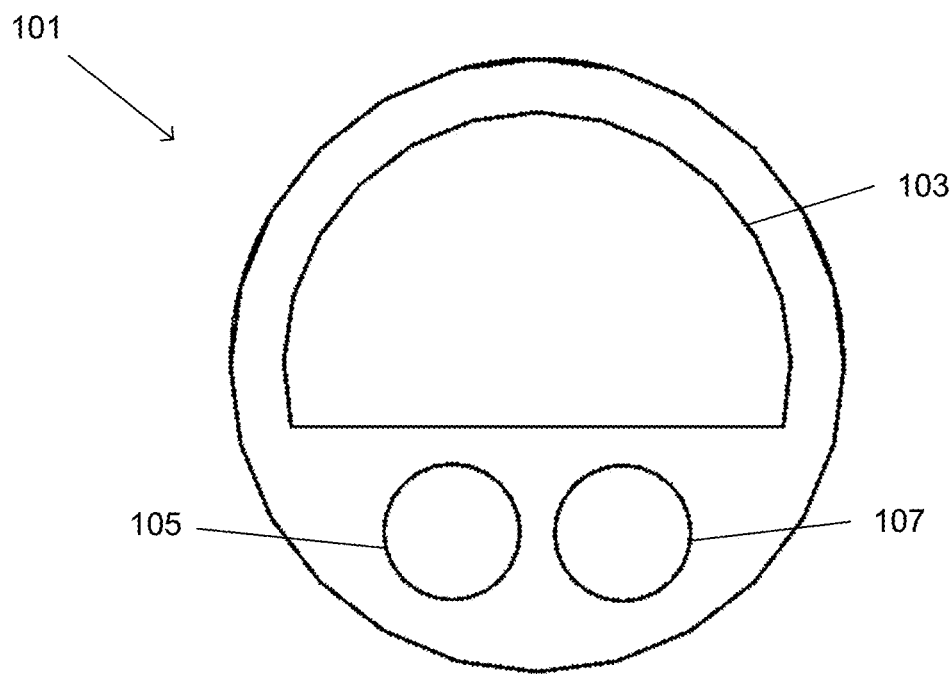
FIG. 4C is a cross-sectional view of the inner catheter multi-lumen design with an infusion lumen, a guide wire lumen, and an inflation lumen in one embodiment.
Figure 4D:
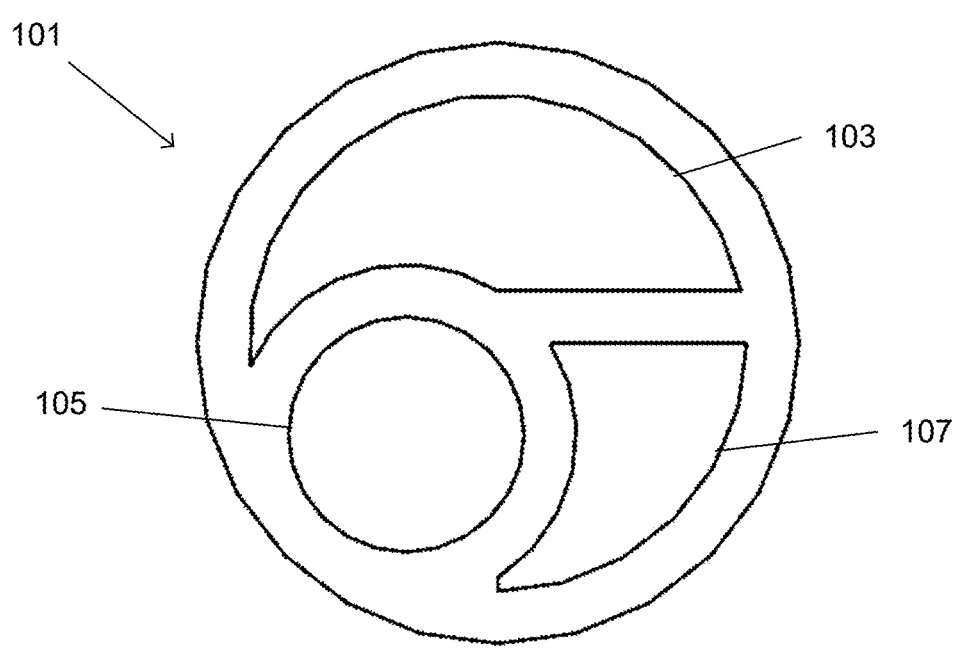
FIG. 4D is a cross-sectional view of the inner catheter multi-lumen design with an infusion lumen, a guide wire lumen, and an inflation lumen in one embodiment.
Figure 4E:
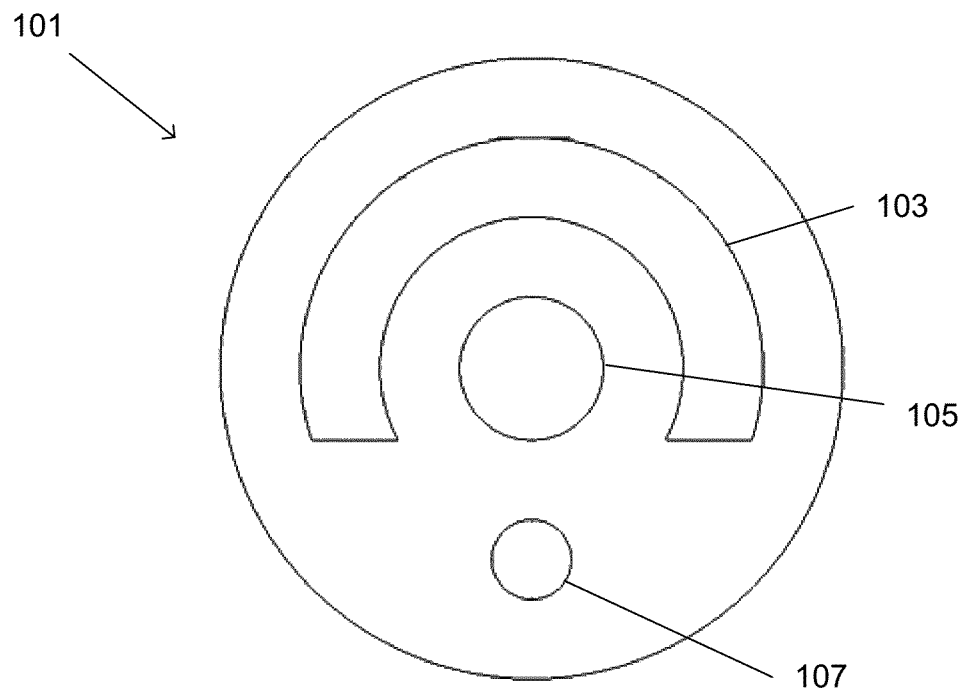
FIG. 4E is a cross-sectional view of the inner catheter multi-lumen design with an infusion lumen, a guide wire lumen, and an inflation lumen in one embodiment.
Figure 4F:
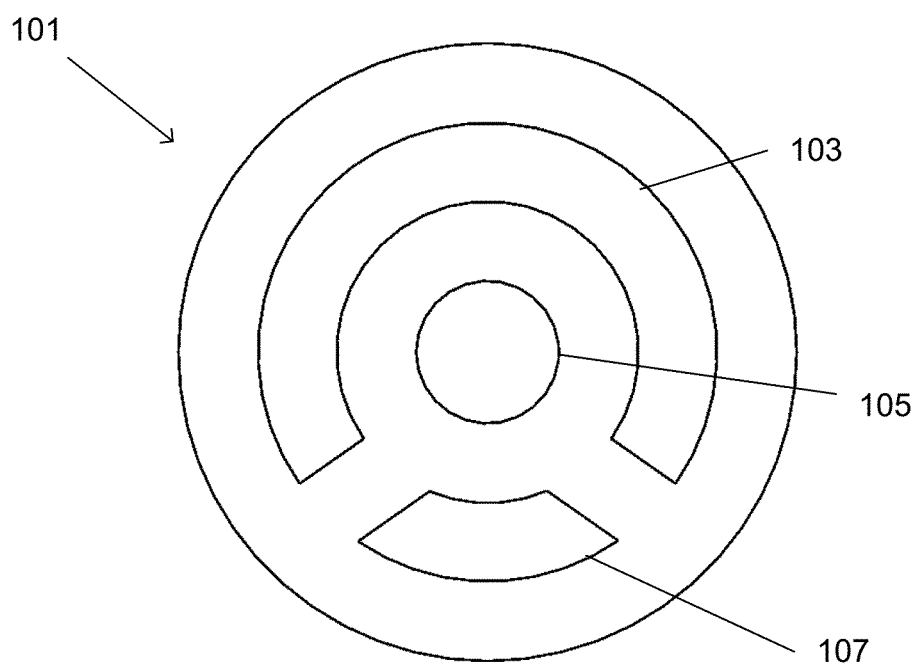
FIG. 4F is a cross-sectional view of the inner catheter multi-lumen design with an infusion lumen, a guide wire lumen, and an inflation lumen in one embodiment.
Figure 4G:
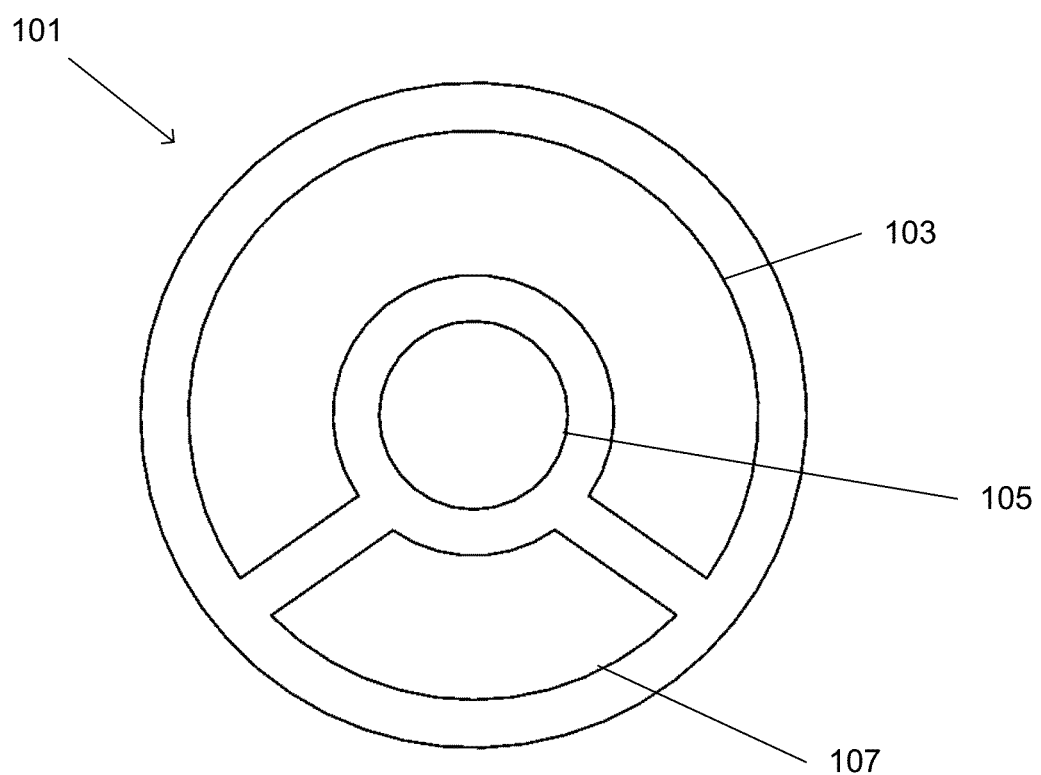
FIG. 4G is a cross-sectional view of the inner catheter multi-lumen design with an infusion lumen, a guide wire lumen, and an inflation lumen in one embodiment.
Figure 5A:
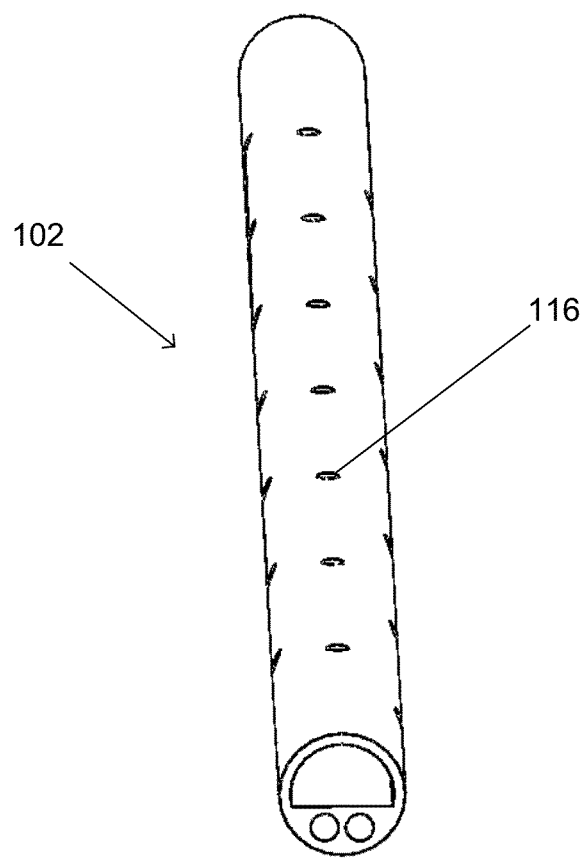
FIG. 5A is an end view of the infusion segment of the inner catheter.
Figure 5B:
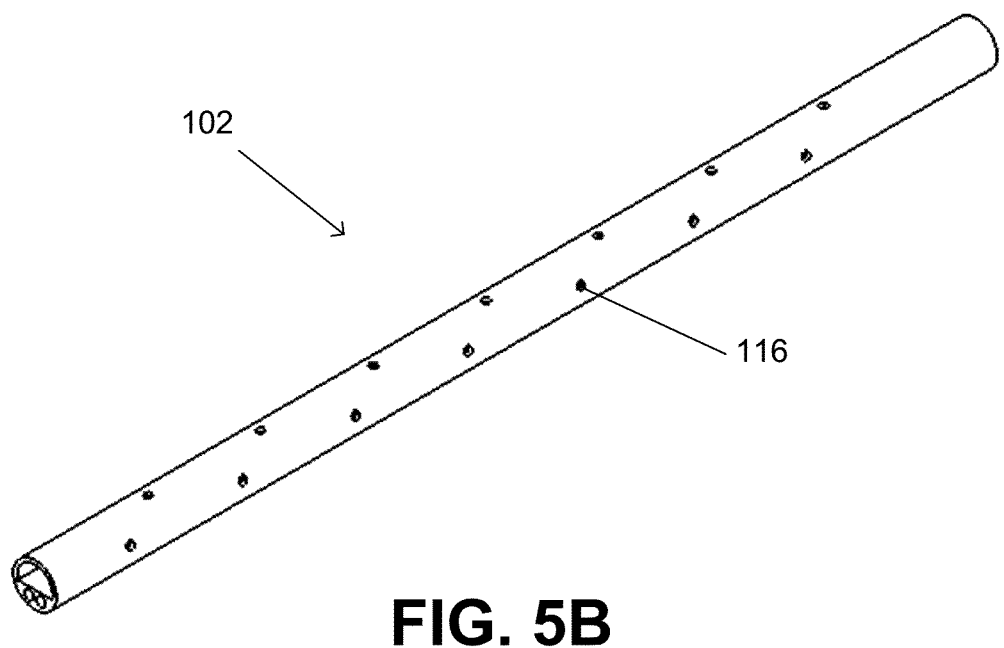
FIG. 5B is an isometric view of the infusion segment of the inner catheter.

FIG. 3 illustrates the inner catheter 101 having a manifold 114, a distal encapsulation balloon 104, and an infusion segment 102 with infusion fenestrations 116. The manifold 114 includes an infusion port 115, balloon inflation port 117, and guide wire access port 119. FIGS. 4A-4G are optional cross-sectional views of the inner catheter 101 multi-lumen design with an infusion lumen 103, a guide wire lumen 105, and an inflation lumen 107. FIGS. 5A and 5B illustrate the infusion segment 102 of the inner catheter 101 with a staggered arrangement of the infusion fenestrations 116.

Figure 7:
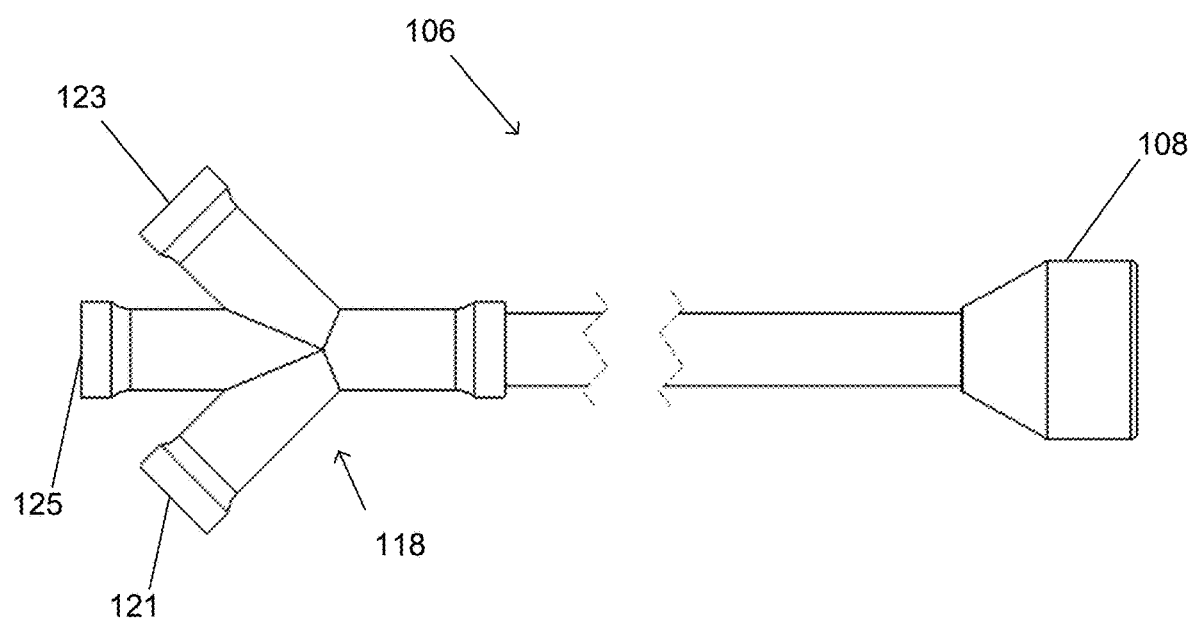
FIG. 7 is a side view the outer sheath that includes a sheath body, an agitator, a proximal balloon, and an outer manifold with a suction port, balloon inflation port, and a device access port in one embodiment.
Figure 8A:
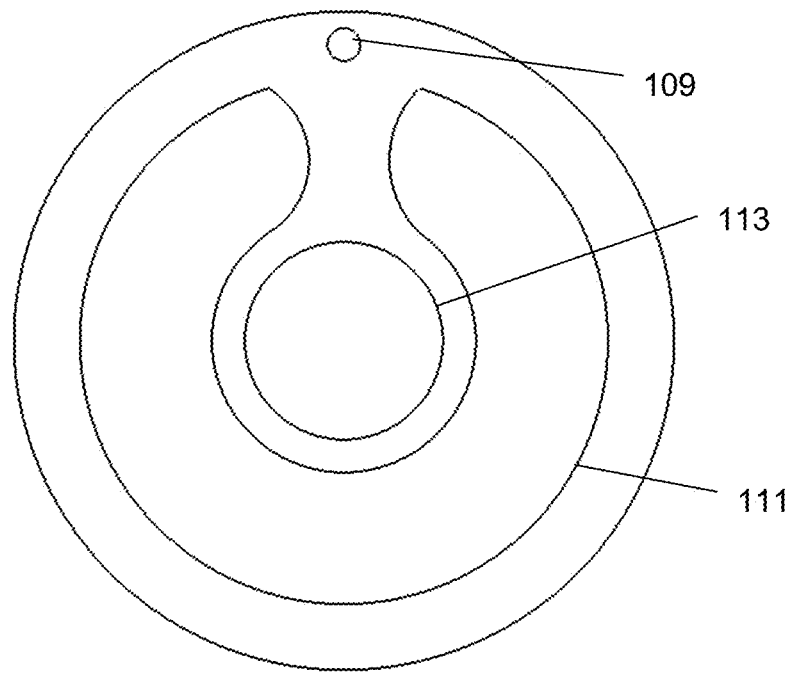
FIG. 8A is a cross-sectional view of the outer sheath multi-lumen design with an inflation lumen, suction lumen, and catheter lumen in one embodiment.
Figure 8B:
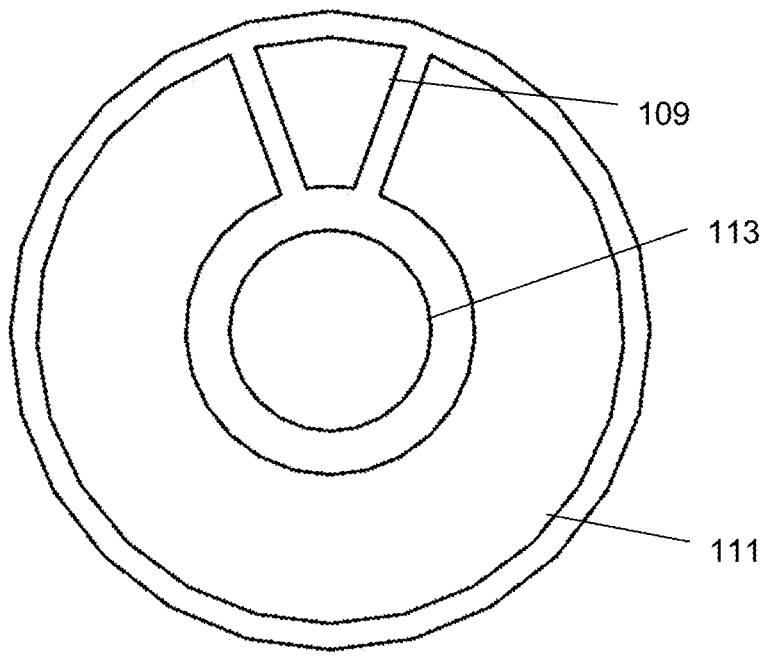
FIG. 8B is a cross-sectional view of the outer sheath multi-lumen design with an inflation lumen, suction lumen, and catheter lumen in one embodiment.
Figure 8C:
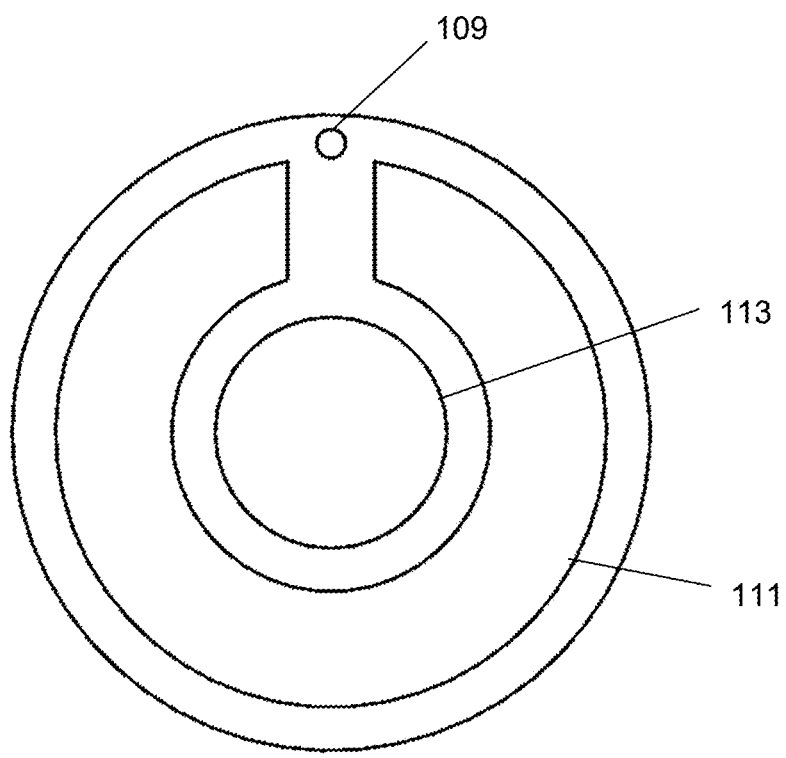
FIG. 8C is a cross-sectional view of the outer sheath multi-lumen design with an inflation lumen, suction lumen, and catheter lumen in one embodiment.
Figure 10:
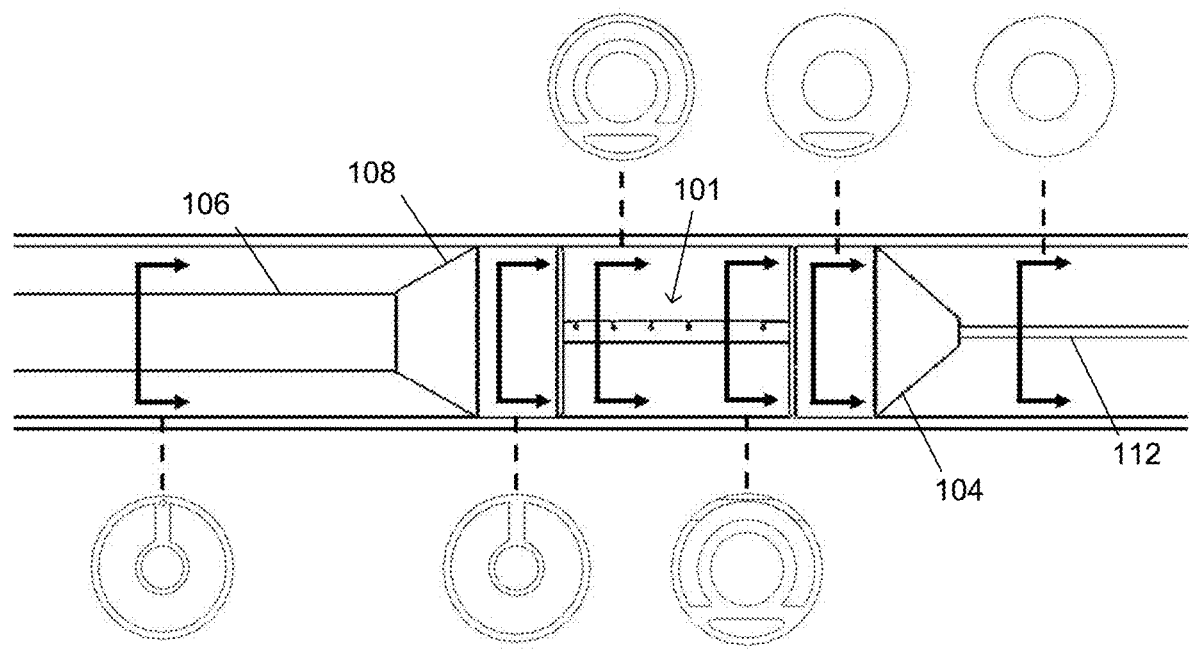
FIG. 10 is a side view of the catheter system in a vein with cross-sectional views along the length of the catheter.

FIG. 7 illustrates the outer sheath 106 that includes an outer manifold 118, a sheath body 120, an agitator 110, and a proximal balloon 108. The outer manifold 118 may include a suction port 121, balloon inflation port 123, and a device access port 125. FIG. 8A-8C are cross-sectional views of the outer sheath 106 multi-lumen design with an inflation lumen 109, suction lumen 111, and catheter lumen 113. FIGS. 3A-3G are examples of the agitator 110 that advance and retract over the outer sheath inner lumen housing the inner catheter. FIG. 10 illustrates the catheter system within a vessel and provides cross-sections of the inner catheter and outer sheath at various points along the catheter system.

Figure 11:
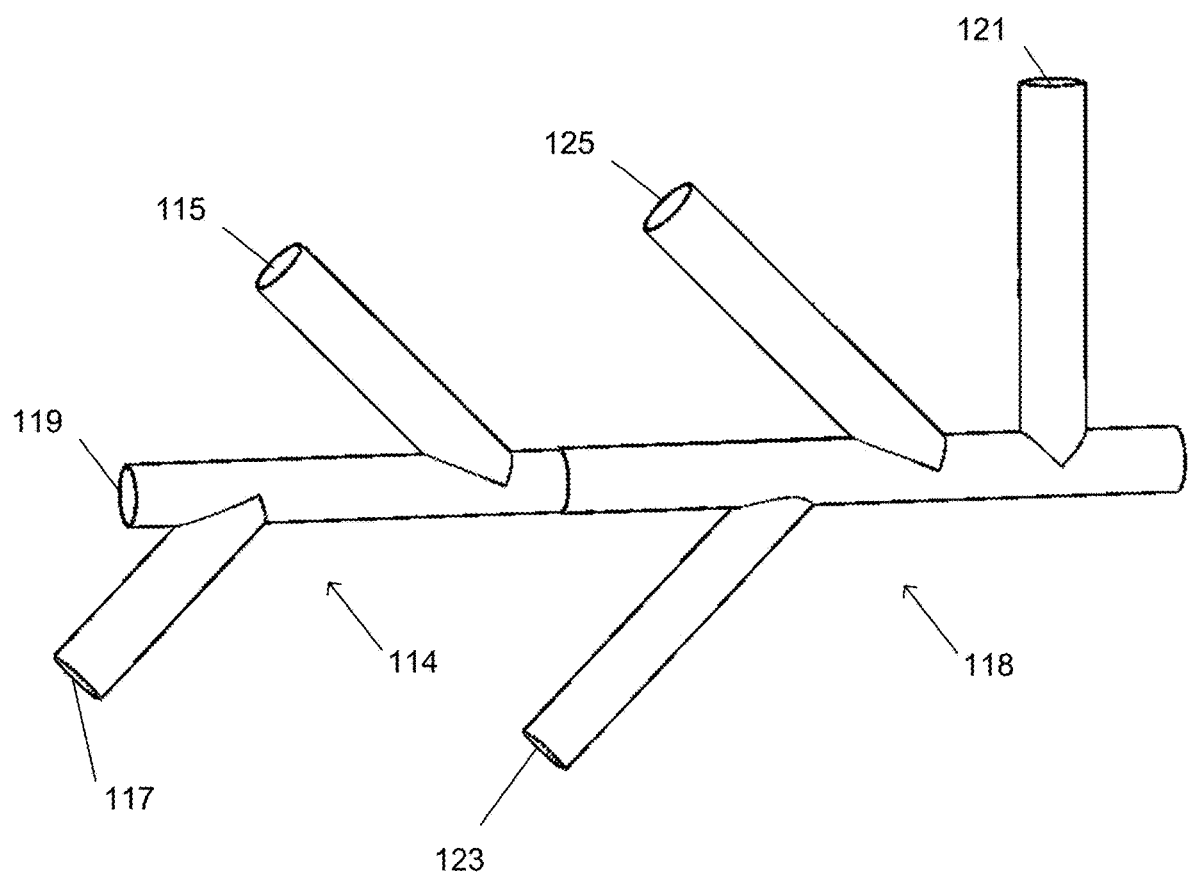
FIG. 11 is a side view of a combined manifold for the inner catheter and outer sheath.

In some examples, the manifold 114 for the inner catheter and the outer manifold 118 for the outer sheath may be connected together to form one combined manifold, as seen in FIG. 11. The various ports may be operated as follows. The guidewire is advanced through the guidewire port through the thrombus ahead of the catheter system. With all ports sealed, the catheter system is moved into position proximal to the thrombus. The proximal balloon inflation port 123 is opened and the proximal encapsulation balloon 108 is inflated. The proximal balloon inflation port 123 is then closed. A Tuohy Valve sealing the inner catheter is released, and the inner catheter is advanced distal to the thrombus (4 cm of treatment zone length). The inner catheter Tuohy Valve is then sealed. The distal balloon inflation port 117 valve is opened and the distal balloon 104 is inflated. The distal balloon inflation valve is then closed.

The order of the following operations may be based upon the discretion of the operator, with the option to mechanically and/or chemically agitate the thrombus made available. The infusion port 115 and suction port 121 valves may be opened, and lytics may be infused through the infusion port 115 while the same quantity of fluid may be removed via the suction port 121 to maintain isovolumetric conditions within the treatment area. The suction and infusion ports 121, 115 may both be closed, and the mechanical agitator 110 may be moved along the treatment area through the device access port 125. In some examples, the device access port may be a push-rod Tuohy Valve.

Based on the discretion of the operator, these steps may be repeated any number of times, possibly with the infusion of saline solution through the infusion ports to ensure no lytics remain in the patient following removal of the catheter system. The distal balloon inflation port 117 is opened, and the distal balloon 104 is deflated. The distal balloon inflation port 117 is then closed. The Tuohy Valve at the device access port 125 is opened, and the inner catheter 101 is retracted into the outer sheath 106. The Tuohy Valve is then closed. The proximal balloon inflation port 123 is opened, the proximal balloon 108 is deflated, and the proximal balloon inflation port 123 is closed. The catheter system is retracted along the guidewire and removed from the patient. The guidewire is then removed, completing the procedure.

The catheter system can be operated percutaneously and introduced intravenously using the Seldinger technique (a method of introducing catheters and catheter-based devices into vessels from outside of the body over a wire). In an embodiment, the catheter system may be flexible to facilitate advancement from either a femoral vein cannulation or internal jugular vein cannulation.

Micro- and macro-emboli during venous thrombectomy procedures can be especially dangerous and can lead to fatal PE. The use of a typical thrombectomy device has been shown to create upwards of 300,000 particles sized 10-100 um, ~1,000 particles sized 100-1,000 um, and ~20 particles larger than 1 mm. In an embodiment, the catheter system proximal and distal balloon encapsulation design minimizes thrombus particle embolization.

As seen in FIGS. 1, 2A, and 2B, the catheter system has a tandem balloon encapsulation design with proximal and distal encapsulation balloons that conform around the intraluminal thrombus. This adjustable dual balloon design maintains cradling and entrapment of the intraluminal thrombus to reduce the risk of intra-procedural thrombus embolization, facilitate corralling of the thrombus into the proximal suction port of the device, reduce the risk of imprecise treatment of specific venous segments and systemic leakage of thrombolytic agents, and minimize trauma to the vessel wall.

The adjustability of the distance between the proximal and distal encapsulation balloons allows for adjustability of the thrombolytic treatment area between the balloons. In some examples, the distance between the proximal and distal encapsulation balloons is determined based on how far the inner catheter is permitted to extend beyond the outer sheath. The treatment area is then set by the inflation of both the proximal and distal encapsulation balloons. This also locks the catheter system in place within the vessel. In various examples, the treatment area length may range from about 1 cm to about 25 cm. In one example, the treatment area may have a length of about 4 cm. The thrombus to be removed is contained within the thrombolytic treatment area. In addition, the infusion segment of the inner catheter is within the thrombolytic treatment area. The variable length of the treatment area allows for the accommodation of a range of clot geometries and provides freedom to treat a clot in a staged fashion.

The catheter system may further facilitate release of a fluid through the infusion segment of the inner catheter. In some examples, the fluid may contain thrombolytics and/or contrast agents. In an embodiment, the thrombolytics may be infused through infusion fenestrations in an infusion segment of the inner catheter of the catheter system.

The inner catheter and outer sheath are operable to provide isovolumetric suction and restoration of fluid within the thrombolytic treatment area. For example, the catheter system further utilizes isovolumetric aspiration for the removal of the thrombus from the treatment area. The catheter system includes both an inner catheter infusion port (FIG. 3) and an outer sheath negative suction port (FIG. 7) to allow movement of fluid into and out of the treatment area. The inner catheter infusion port is intended to facilitate both thrombolytic medication administration as well as provide an inflow saline circuit to prevent venous wall collapse during outer sheath negative suction. In an embodiment, the inner catheter may be used as both a thrombolytic infusion catheter as well as a saline infusion port to facilitate isovolumetric thrombus aspiration from the venous treatment area. The outer sheath suction port may have a large aspiration lumen to rapidly evacuate clot fragments and accommodate a range of negative suction strengths.

The catheter system further includes an agitator, such as bristle morcellation to mechanically agitate the thrombus. The built-in agitator/morcellation design may enhance the catheter system's efficiency in thrombus fragmentation and evacuation. The agitator may be used for thrombus engagement, thrombus fragmentation, and pulling the thrombus into the mechanical suction thrombectomy port. The clot agitation may avoid contact, and thus damage to the vessel wall.

Inner Catheter

The catheter system 100 includes an inner catheter 101. The inner catheter has a proximal end, an infusion segment, and a distal end. In an embodiment, the inner catheter includes at least three lumina, at least one infusion fenestration along the infusion segment, and a distal encapsulation balloon at the distal end of the inner catheter. The inner catheter may further include a manifold at its proximal end comprising an infusion port, a balloon inflation port, and a guidewire access port, such that each port is fluidly connected to one of the at least there lumina of the inner catheter.

As seen in FIGS. 4A-4G, the at least three lumina of inner catheter may include, but are not limited to an inflation lumen 107, a guidewire lumen 105, and an infusion lumen 103. These lumina extend from the proximal end to the distal end of the inner catheter and are each fluidly connected to one of the ports at the proximal end of the inner catheter. For example, the inflation lumen is fluidly connected to the balloon inflation port, the guidewire lumen is fluidly connected to the guidewire access port, and the infusion lumen is fluidly connected to the infusion port. In some examples, manifold with the balloon inflation port, the guidewire access port, and the infusion port may be combined with the outer manifold of the outer sheath, as shown in FIG. 11.

FIGS. 4A-4G show example cross sections of the inner catheter. In general, the infusion lumen is the largest of the three lumina in the inner catheter. In some examples, the inner catheter includes a large "D-shaped" infusion lumen and twin lumina beneath it for the guide wire and distal balloon inflation. The guide wire may exit the inner catheter along the centerline and may be the only lumen past the distal balloon.

The inner catheter may have an outer diameter of about 4 French to about 7 French. In one embodiment, the inner catheter has an outer diameter of about 5.5 French. The inner catheter may have a length ranging from about 60 cm to about 160 cm. In one embodiment, the inner catheter has a length of about 100 cm from the distal edge of the manifold to the distal end of the distal encapsulation balloon.

The infusion segment 102 of the inner catheter 101 includes at least one fenestration 116 which is fluidly connected to the infusion lumen to enable infusion of a fluid into the treatment area. In some examples, the fluid is an infusion solution. In an embodiment, an infusion solution that is introduced in the infusion port will travel through the infusion lumen and exit the inner catheter at the at least one fenestration. In some embodiments, the infusion solution is a thrombolytic solution, saline, or combinations thereof. In an embodiment, the infusion solution may be introduced into the inflation port with a syringe.

In an embodiment, the infusion fenestrations have a diameter of about 0.01 inches to about 0.5 inches. In one example, the fenestrations have a diameter of about 0.02 inches. In some examples, the fenestrations have a diameter of less than 0.5 mm. In another example, the fenestrations have a diameter of about 0.4 mm. The number of infusion fenestrations along the length of the infusion segment may vary from about 1 to about 5 fenestrations per cm of the infusion segment. In some examples, the fenestrations may be spaced about 2 mm apart. In one example, treatment area of about 4 cm with 0.4 mm diameter fenestrations spaced 2 mm apart in a staggered formation would result in 21 total fenestrations.

The fenestrations may be in a staggered formation or may be in an ordered formation. The infusion segment may include infusion fenestrations along the right, top, and left planes of the inner catheter. In an example, the infusion fenestrations are separated from one another along each plane equidistant from one another, and are staggered across the three planes by beginning their spacing pattern slightly further on each plane.

In an embodiment, lytics may be infused into a 4 cm-long treatment area along three lines of 0.4 mm outer diameter infusion fenestrations oriented along the top, right, and left planes of the infusion segment of the inner catheter. Along each of the three lines, each fenestration may be separated along its centerline by about 6 mm, while each fenestration may be separated from its counterpart on the adjacent plane by about 2 mm. For example, a fenestration may be present on the right plane, and on the top plane about 2 mm away along the inner catheter's length. This allows for infusion to occur along three planes while maintaining the structural integrity of the inner catheter. These fenestrations run the length of infusion segment in the treatment area, which in concert with the suction lumen in the outer sheath help to maintain isovolumetric conditions by regulating fluid volume in the whole of the treatment area.

The guidewire lumen is configured to receive a guidewire such that the catheter system may be inserted into a patient using standard catheter introducing techniques. In various embodiments, the guidewire lumen has a diameter of about 0.02 inches to about 0.1 inches. In one embodiment, the guidewire lumen has a diameter of about 0.038 inches. In an example, as seen in FIGS. 4A-B and 4E-4G, the guidewire lumen 105 may be concentric with or centrally located within the inner catheter 101. In other examples, the guidewire lumen 105 may be off-center within the inner catheter 101.

The inflation lumen 107 may be fluidly connected to the distal encapsulation balloon 104 at the distal end of the inner catheter. For example, a fluid may be introduced through the inflation port, travel through the inflation lumen, and inflate the distal encapsulation balloon. In some embodiments, the fluid may be saline, a biocompatible fluid, atmospheric air, and/or pressurized air. In an embodiment, the fluid may be introduced into the inflation port with a syringe.

Figure 6A:
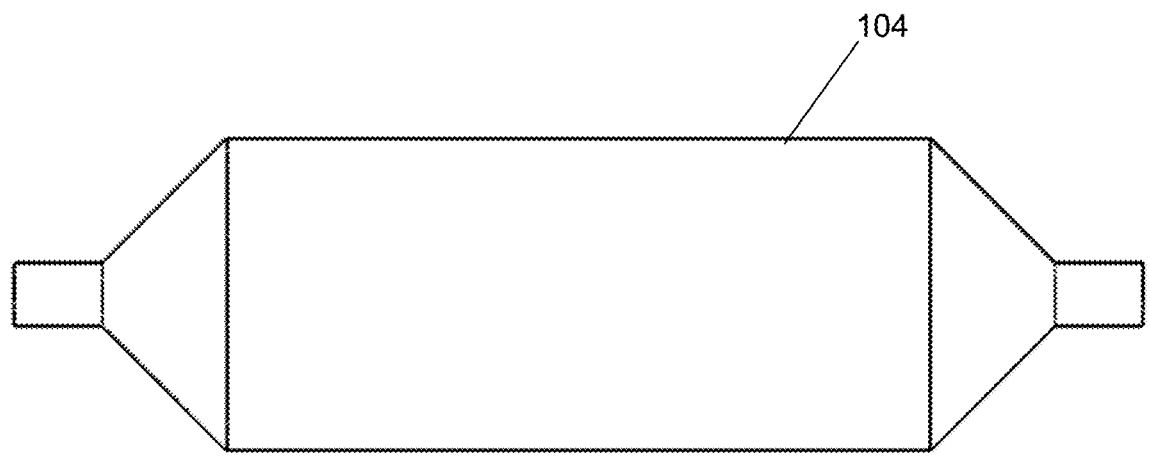
FIG. 6A is a side view of the distal encapsulation balloon of the inner catheter.
Figure 6B:
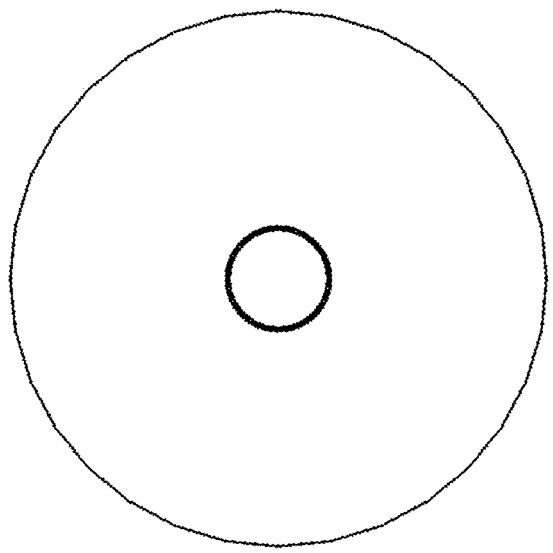
FIG. 6B is a cross-sectional view of the distal encapsulation balloon of the inner catheter.

The distal encapsulation balloon may have an average diameter of about 5 mm to about 30 mm. In one embodiment, the distal encapsulation balloon has a diameter of about 15 mm. The distal encapsulation balloon may have a cylindrical, conical, oval, or circular shape. For example, the distal encapsulation balloon 104 may have a substantially cylindrical shape with tapered ends, as seen in FIGS. 6A and 6B. In some aspects, the distal encapsulation balloon may have a combination of shapes. For example, as seen in FIG. 3, the proximal portion of the distal encapsulation balloon may be substantially cylindrical in shape and the distal portion of the distal encapsulation balloon may have a tapered or conical shape. In various embodiments, the distal encapsulation balloon may have a length of about 1 cm to about 5 cm. In one embodiment, the distal encapsulation balloon may have a total length of about 1.5 cm. In an embodiment, the proximal end of the distal encapsulation balloon may be concave. The distal encapsulation balloon may have a proximal concavity of about 5° to about 15°. In one embodiment, the distal encapsulation balloon may have a concavity of about 10°.

The distal encapsulation balloon may be a compliant balloon operable to accommodate varying vessel sizes and minimize damage or injury to the vessel. The distal encapsulation balloon may be made of polyethylene terephthalate (PET), polyurethane, or any other biocompatible polymer capable of expanding to the appropriate diameters.

Outer Sheath

The catheter system 100 further includes an outer sheath 106 with a proximal encapsulation balloon 108, as seen in FIG. 7. The outer sheath has a proximal end and a distal end. In an embodiment, the outer sheath includes at least three lumina extending from the proximal end to the distal end of the outer sheath, and a proximal encapsulation balloon 108 at the distal end. The outer sheath further includes a manifold 118 at its proximal end with a suction port 121, a balloon inflation port 123, and a device access port 125, such that each port is fluidly connected to one of the at least there lumina of the outer sheath. The outer sheath may have a roughly "power symbol" design, with consistent wall thicknesses to ensure structural stability and a larger lumen for the balloon in the "rail" riding along the length of the outer sheath.

As seen in FIGS. 8A-8C, the outer sheath may include an inflation lumen 109, a suction lumen 111, and a catheter lumen 113. These lumina extend from the proximal end to the distal end of the outer sheath and are each fluidly connected to one of the ports at the proximal end of the outer sheath. For example, the inflation lumen is fluidly connected to the balloon inflation port, the suction lumen is fluidly connected to the suction port, and the catheter lumen is fluidly connected to the device access port.

The outer sheath may have an outer diameter of about 10 French to about 26 French. In one embodiment, the outer sheath has an outer diameter of about 20 French. In another embodiment, the outer sheath may have an inner diameter of about 18 French. The outer sheath may have a length ranging from about 50 cm to about 150 cm. In one embodiment, the outer sheath has a length of about 65 cm from the distal edge of the manifold to the distal end of the proximal encapsulation balloon. In some embodiments, the outer sheath has a length that is shorter than the inner catheter. For example, only a portion of the inner catheter is covered by the outer sheath. This allows for the distal encapsulation balloon on the inner catheter and the proximal encapsulation balloon on the outer sheath to surround a thrombus within a treatment area.

The catheter lumen is configured to receive the inner catheter such that the at least a portion of the inner catheter is surrounded by the outer sheath. In this embodiment, the proximal portion of the inner catheter, before the infusion segment, is covered by the outer sheath. In various embodiments, the catheter lumen has a diameter of about 4 French to about 22 French. In one embodiment, the catheter lumen has an inner diameter of about 5.5 French. The catheter lumen may have an outer diameter of about 7.5 French. In an embodiment, as seen in FIGS. 8A-8C, the catheter lumen may be concentric with or centrally located within the outer diameter of the outer sheath. The inner catheter may be inserted into the catheter lumen at the device access port.

The inflation lumen may be fluidly connected to the proximal encapsulation balloon at the distal end of the outer sheath. For example, a fluid may be introduced through the inflation port, travel through the inflation lumen, and inflate the proximal encapsulation balloon. In some embodiments, the fluid may be saline, a biocompatible fluid, atmospheric air, or pressurized air. In an embodiment, the fluid may be introduced into the inflation port with a syringe. In various embodiments, the inflation lumen may have a diameter of about 1 French to about 4 French. In one embodiment, the inflation lumen has a diameter of about 2 French.

Figure 9A:
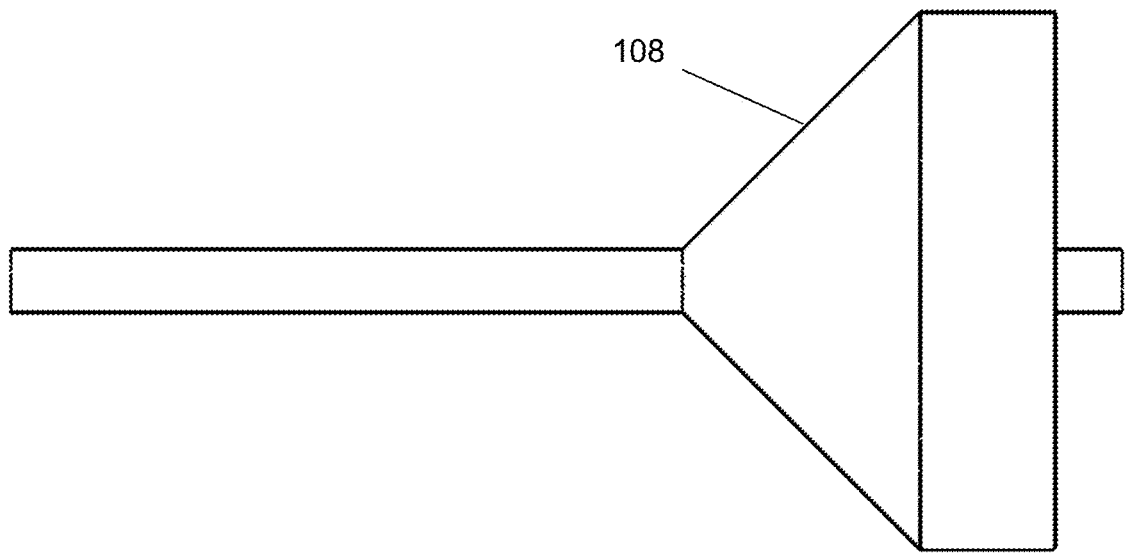
FIG. 9A is a side view of the distal encapsulation balloon of the inner catheter.
Figure 9B:
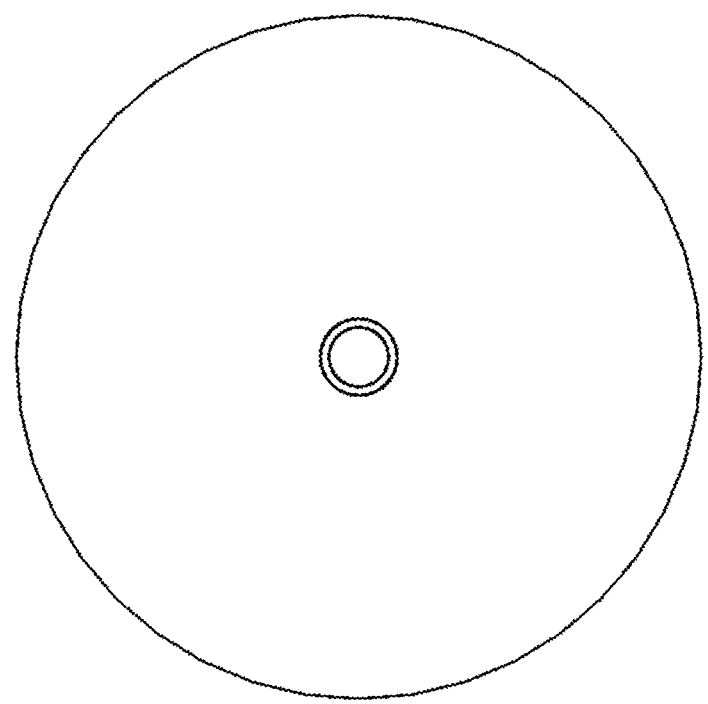
FIG. 9B is a cross-sectional view of the distal encapsulation balloon of the inner catheter.

The proximal encapsulation balloon may have an average diameter of about 10 mm to about 30 mm. In one embodiment, the proximal encapsulation balloon has a diameter of about 15 mm. The proximal encapsulation balloon may have a cylindrical, conical, oval, or circular shape. In some aspects, the proximal encapsulation balloon may have a combination of shapes. For example, as seen in FIGS. 9A and 9B, the distal portion of the proximal encapsulation balloon 108 may be cylindrical in shape and the proximal portion of the proximal encapsulation balloon may have a tapered or conical shape. In various embodiments, the proximal encapsulation balloon may have a length of about 1 cm to about 3 cm. In one embodiment, the proximal encapsulation balloon may have a total length of about 1.5 cm. In an embodiment, the distal end of the proximal encapsulation balloon may be concave. The distal encapsulation balloon may have a proximal concavity of about 5° to about 15°. In one embodiment, the distal encapsulation balloon may have a proximal concavity of about 10°. The proximal encapsulation balloon may be made of polyethylene terephthalate (PET), polyurethane, or any other biocompatible polymer capable of expanding to the appropriate diameters.

The suction lumen may surround the catheter lumen. In various embodiments, the suction lumen may have a diameter of about 11 French to about 22 French. In one embodiment, the suction lumen has a diameter of about 18 French. The suction lumen is fluidly connected to the suction port such that a negative suction can be applied to the suction port and draw up material in the treatment area at the opening of the suction lumen at the distal end of the outer sheath. In various embodiments, the suction applied may range from about 0 kPa to about 150 kPa. In some examples, the suction applied may range from about 0 kPa to about 15 kPa. The suction applied through the suction lumen is balanced with the infusion of the infusion solution through the infusion fenestrations.

Agitator

The catheter system may provide localized mechanical thrombolysis using an agitator operable to agitate or morcellate the thrombus. Morcellation can be used to locally fragment the thrombus. The agitator may be used to mechanically break apart a large thrombus to allow it to be either suctioned through the suction lumen or contained between the proximal and distal encapsulation balloons as the catheter system is removed from the patient.

As seen in FIGS. 1 and 2B, the agitator may extend from the distal end of the outer sheath and into the treatment area to morcellate the thrombus. In some embodiments, the outer sheath encloses the agitator. In an embodiment, the agitator advances and retracts over the catheter lumen of the outer sheath. For example, the agitator may be rail mounted on the outside of the catheter lumen and the inner catheter to maintain its movement along the centerline of the vasculature. In this example, the agitator may be within the suction lumen when retracted within the outer sleeve. In some examples, the agitator is operable to be used without touching a wall of the vessel. FIGS. 13A-13E show end views or cross-sections of various agitators 110 rail mounted on the outer diameter of the catheter lumen 113 of the outer sheath, such that it is inside the suction lumen 111 when retracted.

Figure 14:
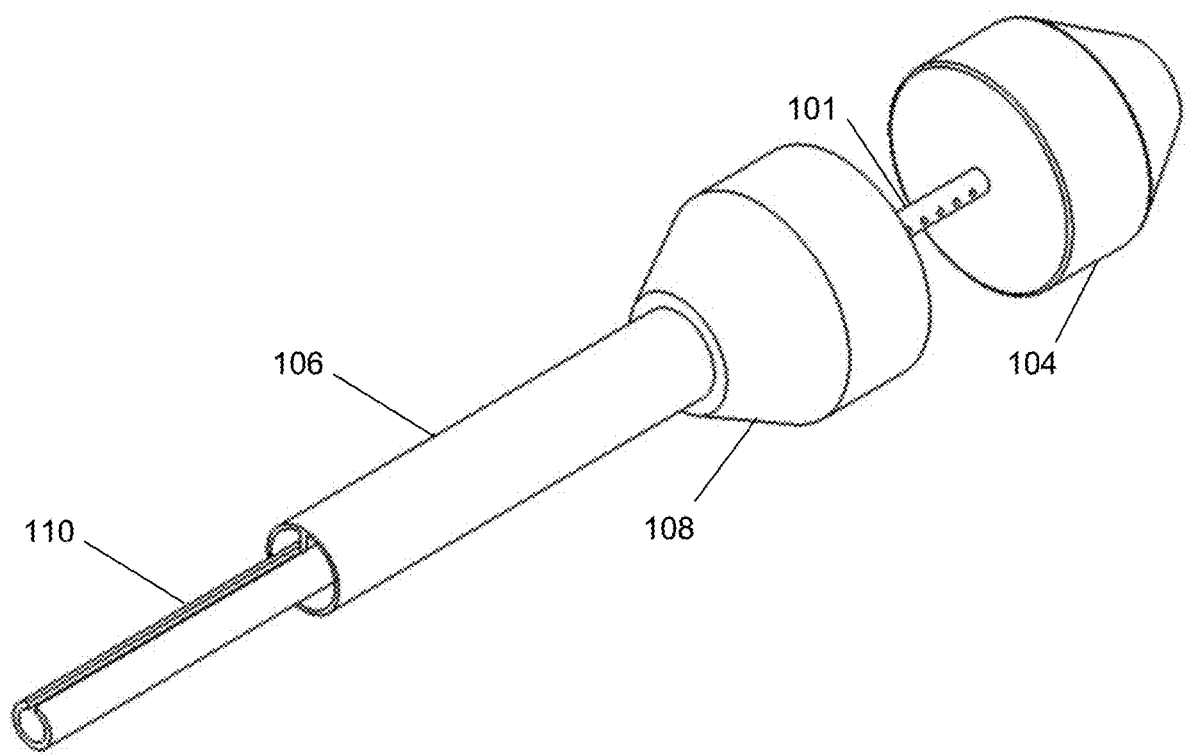
FIG. 14 is an isometric view of the catheter system on one embodiment.

In an embodiment, the agitator may include a plurality of radially extending protrusions from a central ring. The protrusions may be fins, bristles, rod-like, cylindrical, rectangular, or curved. In one embodiment, as seen in FIGS. 12A-12K, the agitator protrusions may be fins, rod-like, or cylindrical. The protrusions may be distributed helically along the length of the agitator. In an embodiment, the central ring is a partial ring and partially surrounds the catheter lumen to enable the rail mounting of the agitator. In some examples, the protrusions are located at the distal end of the central ring and the central ring extends a length along the outer sheath to enable actuation or deployment of the actuator, as seen in FIG. 14. In some examples, the agitator may have a length of at least about 15 cm.

The protrusions may have a radially extending length of about 1 mm to about 5 mm. In some examples, the protrusions may be at a pitch angle operable to reduce shear stress on the vessel. The pitch angle may range from about 5 degrees to about 65 degrees. In one example, the pitch angle may be about 30 degrees. In another example, the pitch angle may be about 15 degrees. In an embodiment, the protrusion density and angle can be optimized to enhance the mechanical traction that the protrusions apply to the thrombus so as to enhance its morcellation.

Figure 12A:
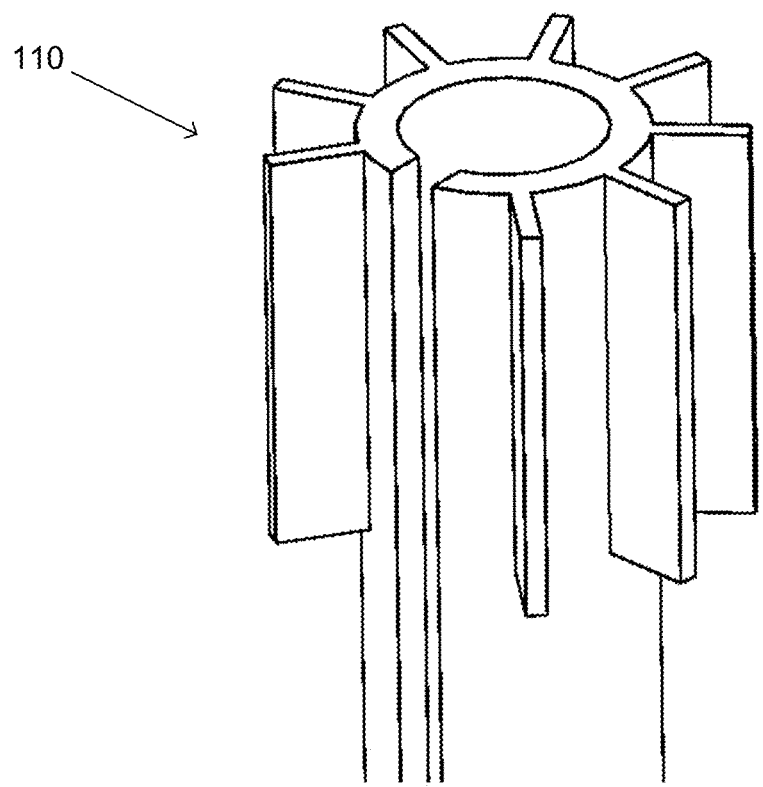
FIG. 12A is a side view of an agitator in one embodiment.
Figure 12B:
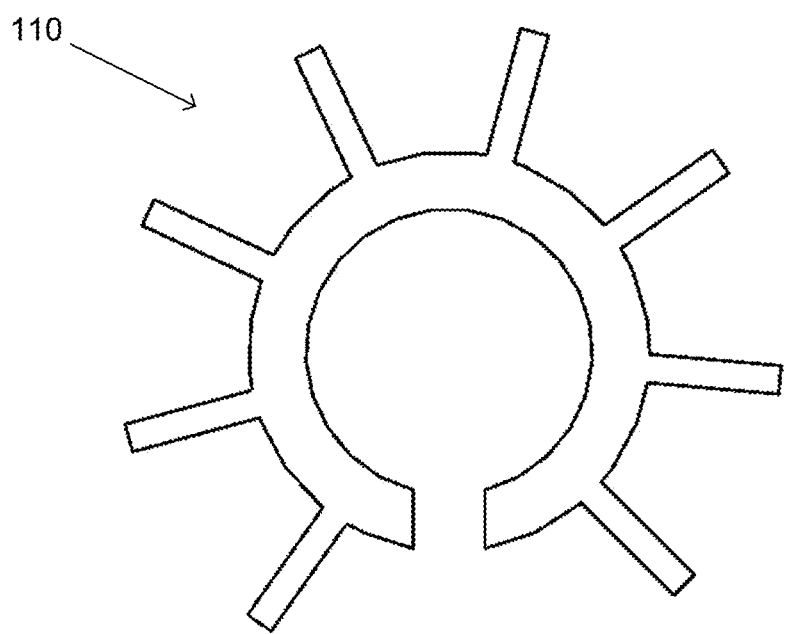
FIG. 12B is a cross-sectional view of an agitator in one embodiment.
Figure 12C:
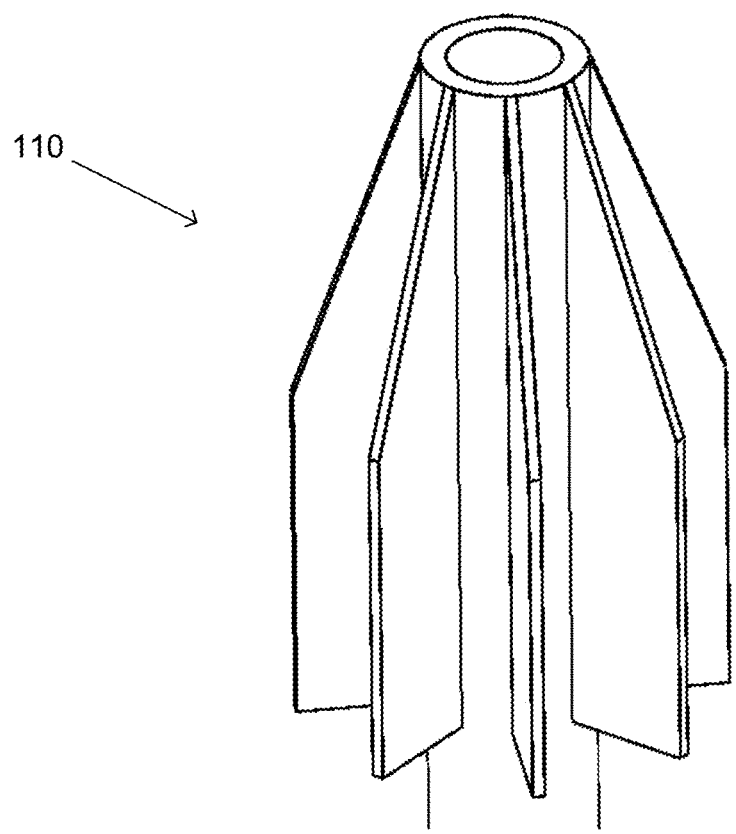
FIG. 12C is a side view of an agitator in one embodiment.
Figure 12D:
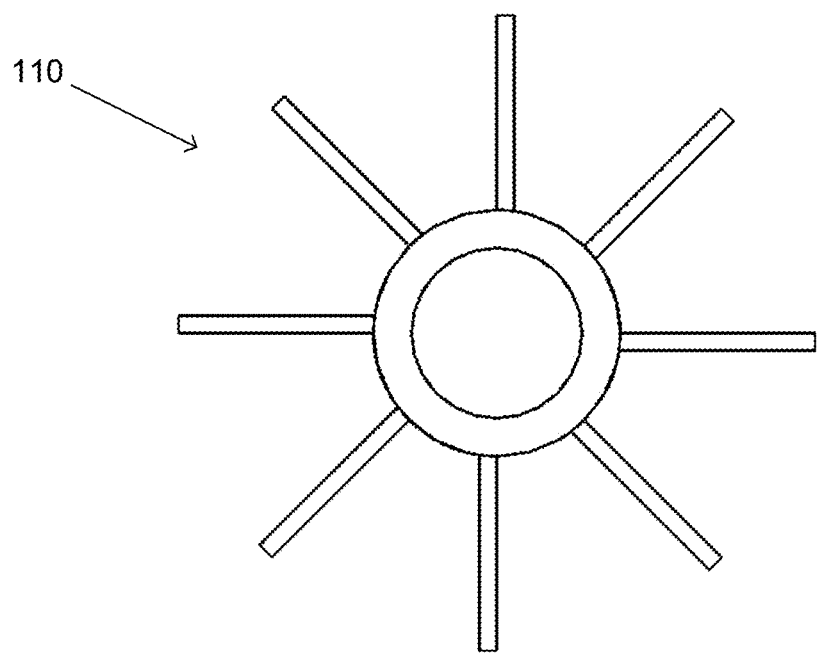
FIG. 12D is a cross-sectional view of an agitator in one embodiment.
Figure 12E:
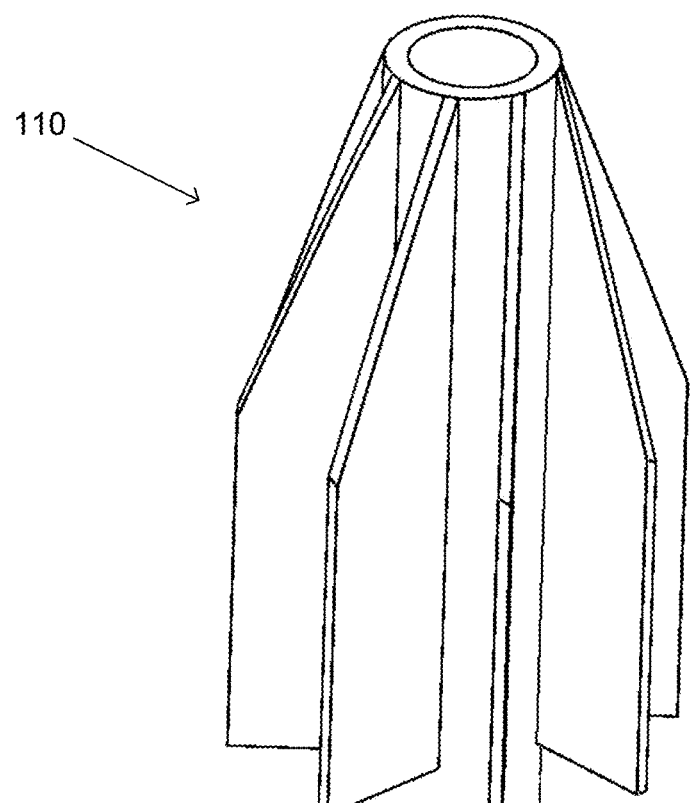
FIG. 12E is a side view of an agitator in one embodiment.
Figure 12F:
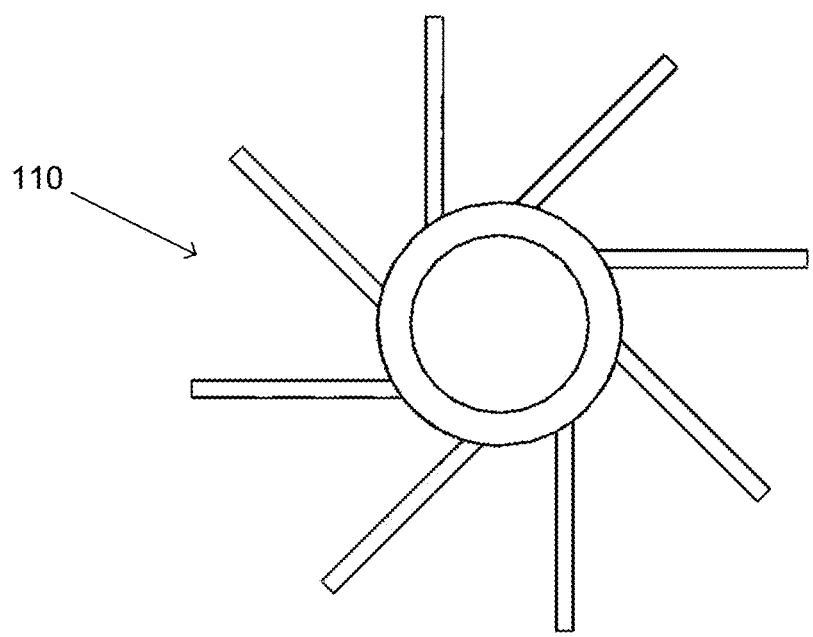
FIG. 12F is a cross-sectional view of an agitator in one embodiment.
Figure 12G:
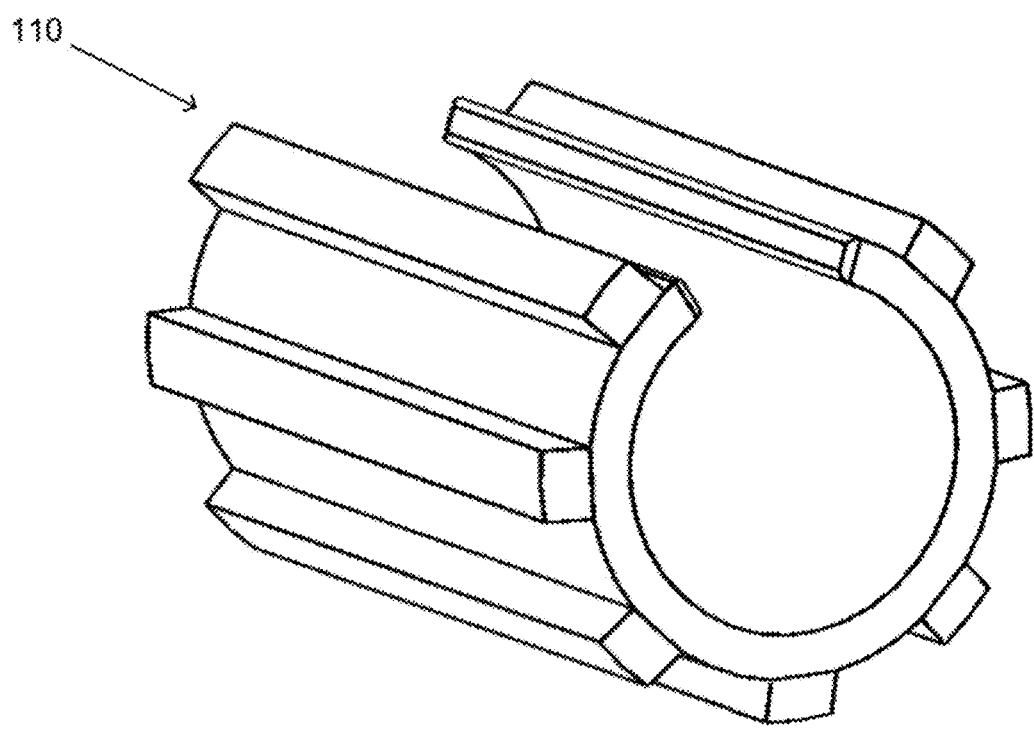
FIG. 12G is an isometric view of an agitator in one embodiment.
Figure 12H:
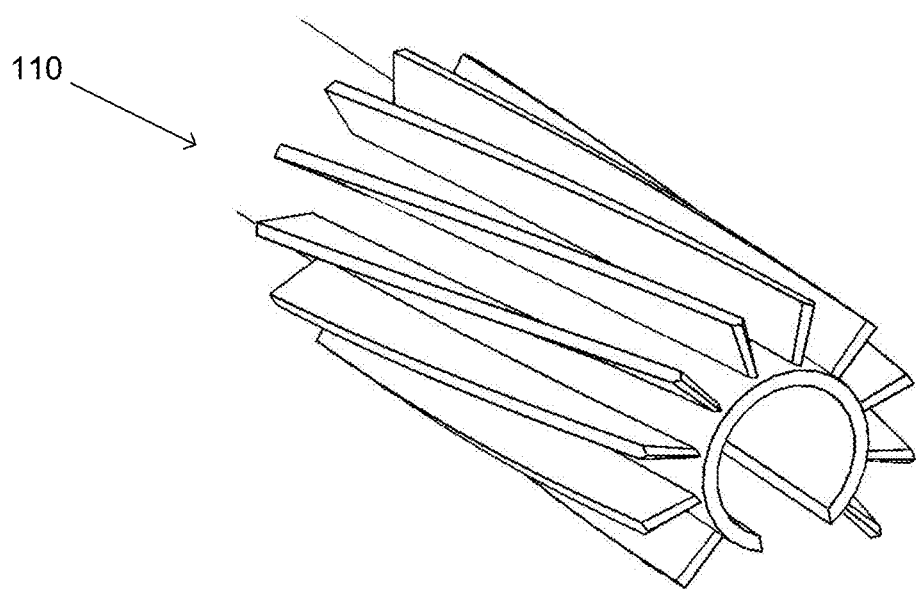
FIG. 12H is a perspective view of an agitator in one embodiment.
Figure 12I:
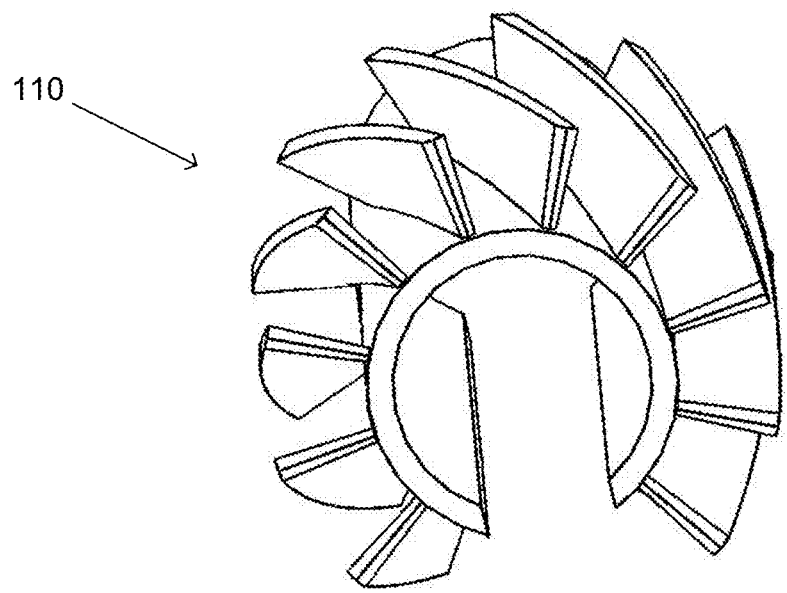
FIG. 12I is a perspective view of an agitator in one embodiment.
Figure 12J:
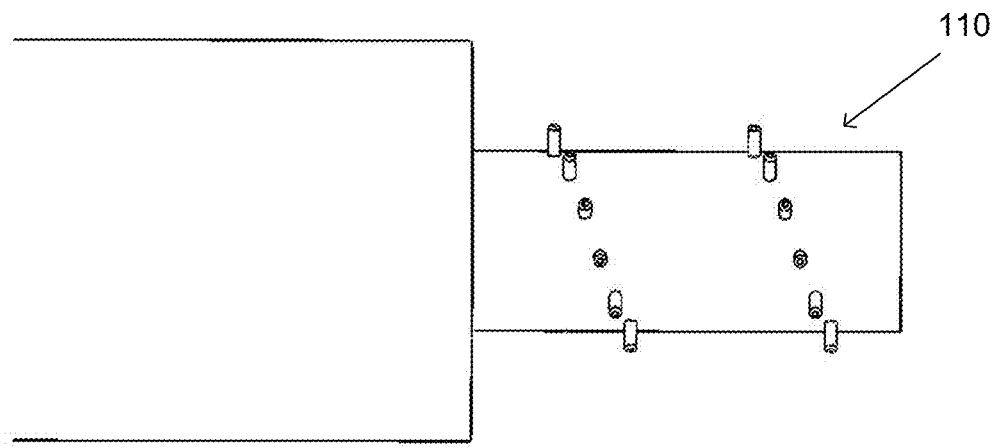
FIG. 12J is a side view of an agitator in one embodiment.

In some examples, the protrusions may be fins extending along a length of the central ring, as seen in FIGS. 12A-12G. In some examples, the fins may be tapered towards the distal end of the agitator or have a cone-like appearance, as seen in FIGS. 12C-12F. Agitator fins may be 5, 10, 15, 20, 25, 30, or 90 degrees relative to the central curve of the longitudinal axis. For example, FIGS. 12A-12D show fins with 0 degree pitch angle and FIGS. 12E-12F show fins with a 30 degree pitch angle. In some examples, the fins may be rolled to have a semi-helical orientation along a length of the central ring, as seen in FIGS. 12H-12I. In additional examples, rod-like protrusions may be staggered along a length of the central ring, as seen in FIG. 12J. The agitator may include variations of the finned (bolt) design, and may be backed with a reinforcing region of similar material. This region may include a "strain release" section in order to allow the agitator to be on the rail within the outer sheath even when fully extended into the treatment area, while also allowing for flexibility in the catheter which may be impeded by a solid agitator of a length of 15 cm or more.

In one example, the mechanical agitator is composed of seven fins, each 0.4 mm in width and 1 mm in height radiating out from a central ring. The finned portion of the agitator may be 1 cm in length, and the front face of each fin may be angled at 20 degrees. Each fin is also "rolled" from the centerline of the agitator at 5 degrees, the combination of these angles having been found to better engage thrombus. The agitator may be connected to the inner catheter which runs along the catheter lumen of the outer sheath by three wires, connected on the left, right, and bottom planes of the agitator. This allows for flexibility in the overall catheter system, as the agitator is able to ride along bends made in the catheter.

Figure 12K:
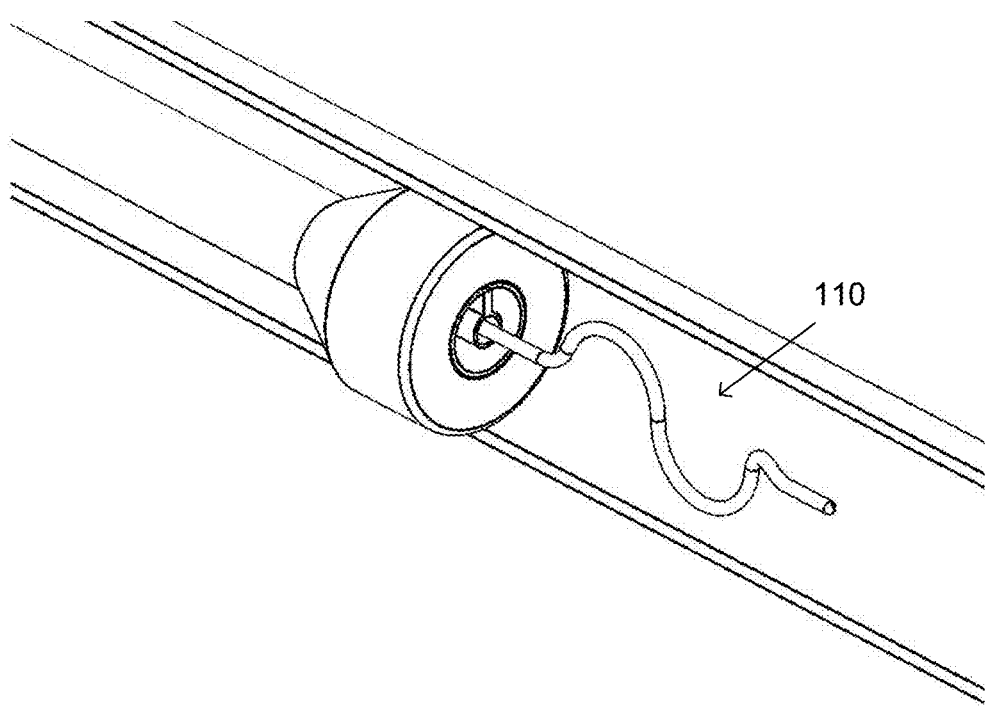
FIG. 12K is a perspective view of an agitator in one embodiment.
Figure 13A:
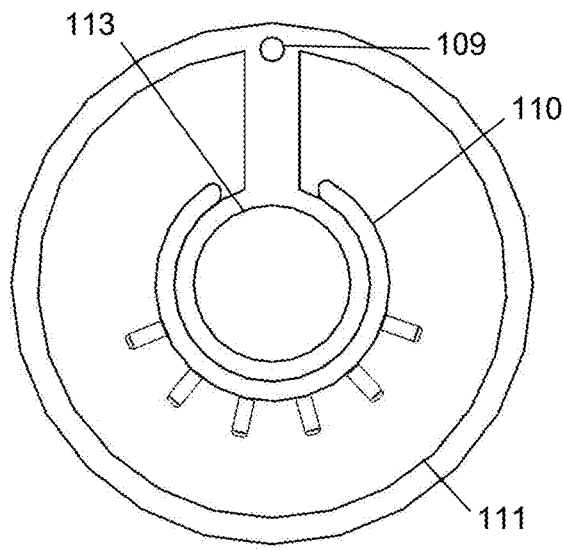
FIG. 13A is a cross-sectional view of an agitator that is designed to advance and retract over the outer device sheath inner lumen housing the inner device catheter in one embodiment.
Figure 13B:
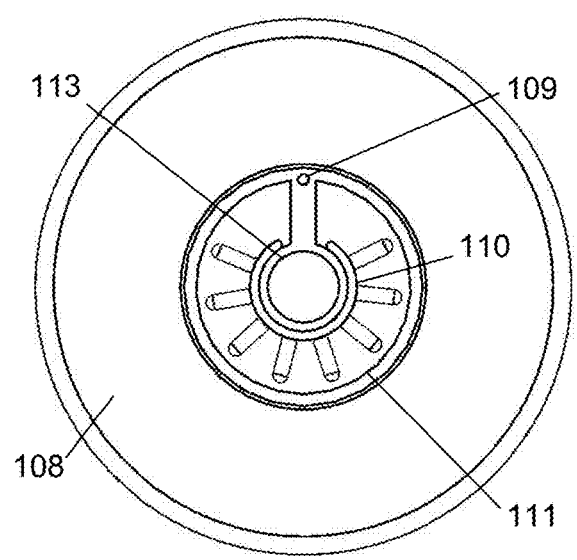
FIG. 13B is a cross-sectional view of an agitator that is designed to advance and retract over the outer device sheath inner lumen housing the inner device catheter in one embodiment.
Figure 13C:
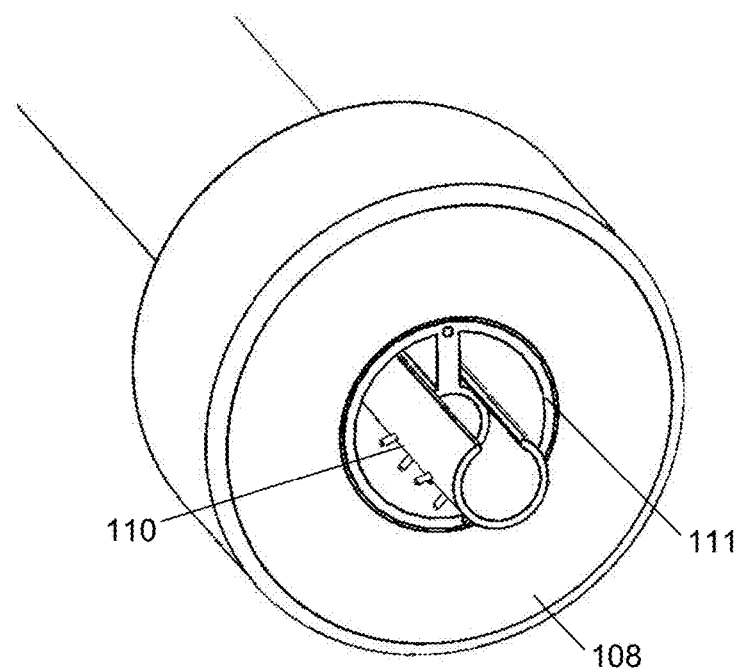
FIG. 13C is a perspective view of an agitator in one embodiment.
Figure 13D:
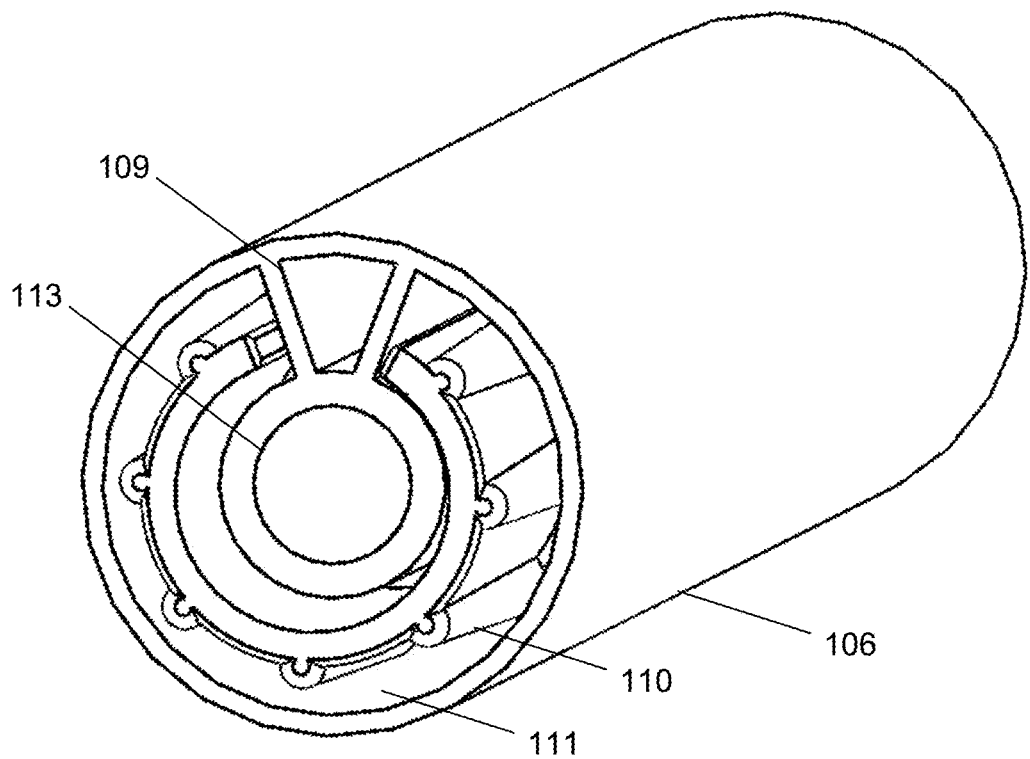
FIG. 13D is a perspective view of an agitator rail mounted on the outer diameter of the catheter lumen of the outer sheath in one embodiment.
Figure 13E:
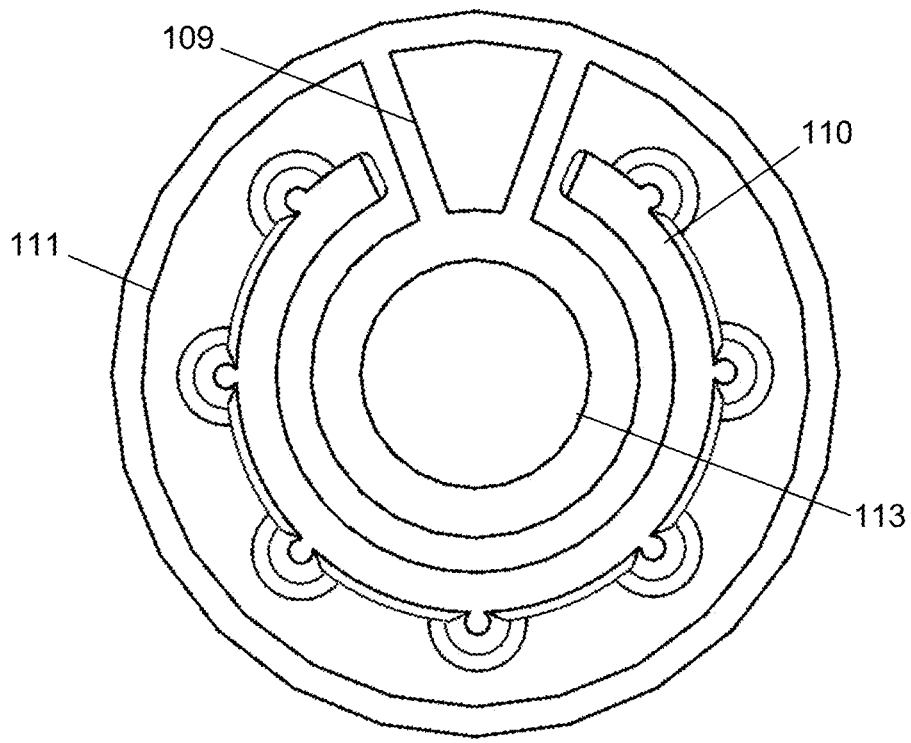
FIG. 13E is a cross-sectional view of the agitator of FIG. 13D.

In another embodiment, the agitator is at least one protrusion or rod extending into the treatment area. For example, the agitator may be a single, curved rod or wire, as seen in FIG. 12K. For example, a cleaner wire may be advanced through the device access port. In this embodiment, the catheter system may only include an outer sheath or catheter, a proximal balloon, and the cleaner wire.

Methods of Thrombus Removal

Provided herein are methods of treatment using the catheter system. In an embodiment, the catheter system is used to treat PE. For example, the catheter system may be advanced from a femoral vein cannulation or internal jugular vein cannulation. The catheter system may then be deployed by inflating the encapsulation balloons, agitating the thrombus, and using isovolumetric suction and restoration of fluid to remove the thrombus.

Further provided herein is a method of removing a thrombus in a patient in need thereof. The method may include inserting the catheter system into a treatment area containing the thrombus. The distal encapsulation balloon may then be inflated through an inflation lumen of the inner catheter and the proximal encapsulation balloon may then be inflated through an inflation lumen of the outer sheath. The inflated distal and proximal encapsulation balloons are inflated such that they encapsulate or surround the thrombus to be removed.

To aid in removal of the thrombus, the method may include localized mechanical thrombolysis using an agitator. Morcellation can be used to locally fragment the thrombus. This may include mechanically moving the agitator in, out, and/or around the treatment area to break apart the thrombus. In one embodiment, morcellating includes advancing and retracting the agitator over the catheter lumen such that the protrusions of the agitator are moved within the treatment area. The catheter system's agitator can be advanced into the thrombosed segment in a controlled fashion.

The method may further include applying isovolumetric suction and restoration of fluid to the treatment area. Localized negative suction may be applied to the treatment area through a suction lumen of the outer sheath. The negative suction may provide for removing at least a portion of the thrombus through the suction lumen. The negative suction may also allow for retaining the thrombus within the treatment area, i.e. between the encapsulation balloons. The suction port may be attached to a negative suction pump capable of delivering a pure vacuum of about 5-40 inHg or about 17-135 kPa. The negative suction pump may be attached to a reservoir canister/bag to collect thrombus. In one embodiment, the reservoir canister/bag may be 1,000 mL.

In various embodiments, the negative suction may be applied for less than about 30 seconds, about 30 seconds, about 1 minute, about 2 minutes, about 5 minutes, or more than 5 minutes. In one embodiment, the negative suction is applied for about 2 minutes. To counter the negative suction within the treatment area, the method may also include infusing an infusion solution to the treatment area through the at least one infusion fenestration. The infusion solution may be a thrombolytic solution, saline, or combinations thereof. The infusion solution may also work in combination with the agitator to break apart the thrombus for removal.

The method may optionally include infusing a thrombolytic through the inner catheter for localized chemical thrombolysis. The infusion fenestrations in the inner catheter may facilitate release of the thrombolytics at the infusion segment or distal end of the inner catheter. In one embodiment, the thrombolytic may be tissue plasmogen activator (tPA). The concentration of thrombolytic may range from about 1 mg/mL to about 40 mg/m L. In various embodiments, the thrombolytic concentration released by the catheter system may be about 1 mg/mL, about 5 mg/mL, about 10 mg/mL, about 20 mg/mL, about 30 mg/mL, or about 40 mg/mL. For example, the tPA concentration may be about 5-20 mg in about 20-200 mL.

The method may further include removing the catheter system from the patient. When the catheter system is removed, the proximal and distal encapsulation balloons may remain inflated such that any remaining portion of the thrombus remains encapsulated between the balloons as the system is removed from the patient. In various embodiments, greater than about 80% luminal patency is restored, greater than about 85% luminal patency is restored, greater than about 90% luminal patency is restored, greater than about 95% luminal patency is restored, or greater than about 99% luminal patency is restored after removal of the thrombus with the catheter system. In an embodiment, greater than about 90% luminal patency of the treatment area is restored.

In other embodiments, a catheter system including an outer sheath/catheter, proximal balloon, and agitator may be utilized. In this embodiment, the outer catheter may be advanced proximal to the thrombus. The proximal balloon may then be inflated to allow for proximal fixation and halting of PA inflow. The agitator (e.g. cleaner wire) may then be advanced through the device access port. Then, negative retrograde suction may be initiated as the cleaner wire is rotated to begin thrombus fragmentation.

Figure 15:
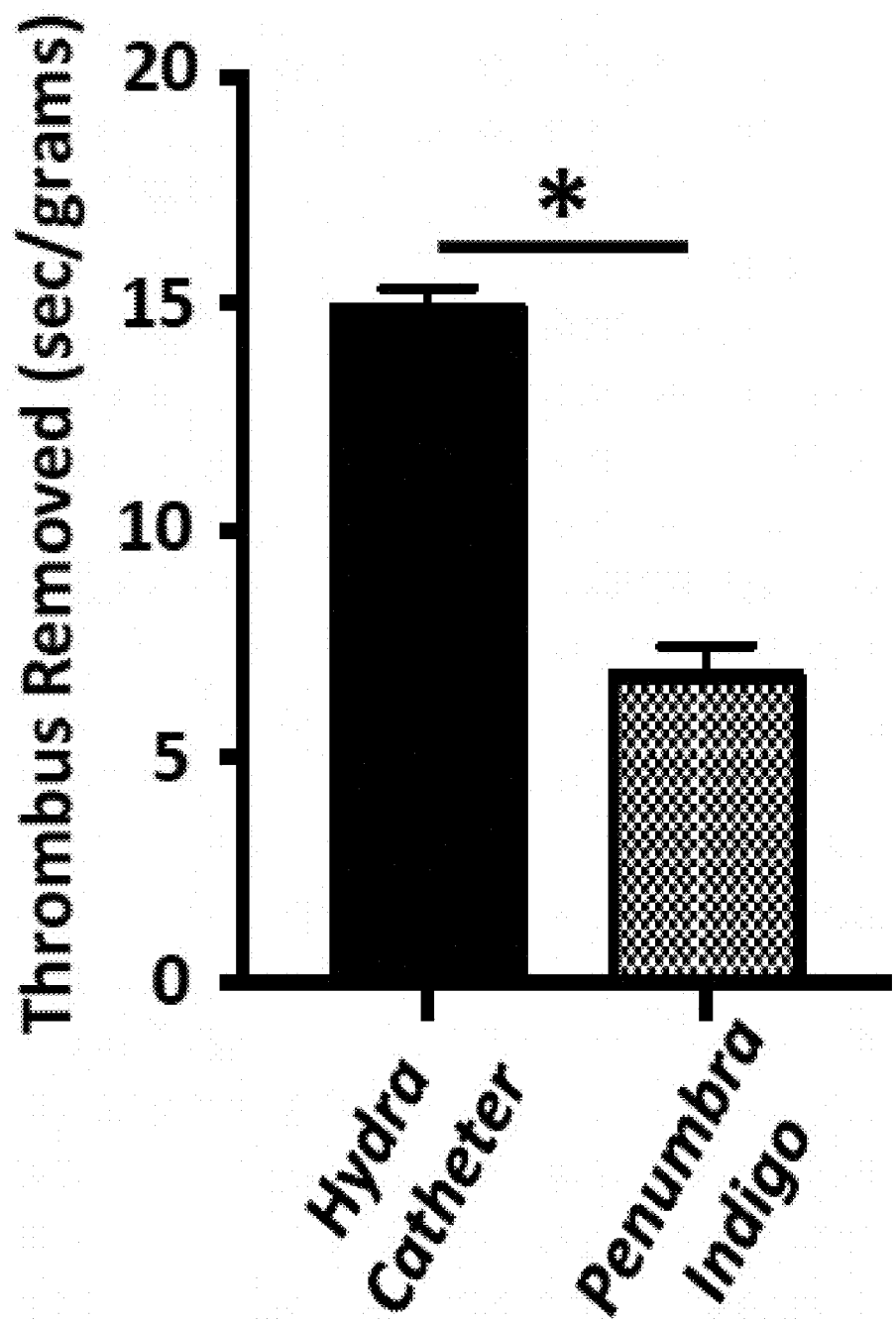
FIG. 15 is a graph comparing the catheter system to the Indigo® Penumbra catheter showing that the catheter system is able to more efficiently remove thrombus in a bench-top thrombectomy experiment. *p<0.01

In an embodiment, the catheter system provides a minimally invasive and efficient removal of 'large-volume' thrombus from the ilio-caval venous segment. In some embodiments, the catheter system provides at least about 90%, at least about 95%, at least about 98%, at least about 99%, or near 100% retrieval of an intravenous thrombus. In an embodiment, the catheter system may minimize the risk of trauma to the venous lumen and endothelium. The catheter system may also have compatibility with existing catheter-based platforms and technology. In an embodiment, the catheter system has the ability to effectively fragment and evacuate an intraluminal thrombus. For example, the Examples below show the catheter system design is superior to the Indigo® catheter in engaging a thrombus and evacuating it (FIG. 15).

EXAMPLES

Example 1

Preliminary Comparative Analysis of Prototype Suction Thrombectomy Efficiency

A balloon encapsulation endovascular thrombectomy catheter system (referred to herein as Hydra) was tested using the methods in the Examples below. Custom-morph polyethylene terephthalate (PET) balloons were developed. A bench-top IVC luminal thrombus model was developed for initial comparative testing between the Hydra catheter and Indigo® Penumbra catheter. 5 cm$^3$ of subacute thrombus was engaged with 70 kPA negative suction using the Hydra catheter and Indigo® Penumbra catheter. Over the course of 1 minute the Hydra catheter was able to more efficiently remove the thrombus (p<0.01; FIG. 15).

Example 2

Agitator Analysis

Figure 16A:
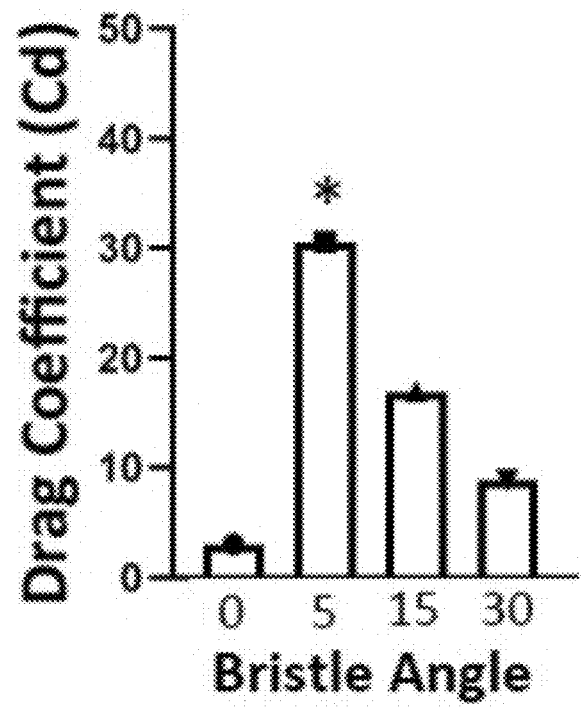
FIG. 16A is a graph of fluent flow simulation drag coefficient at various bristle angles. *p<0.01
Figure 16B:
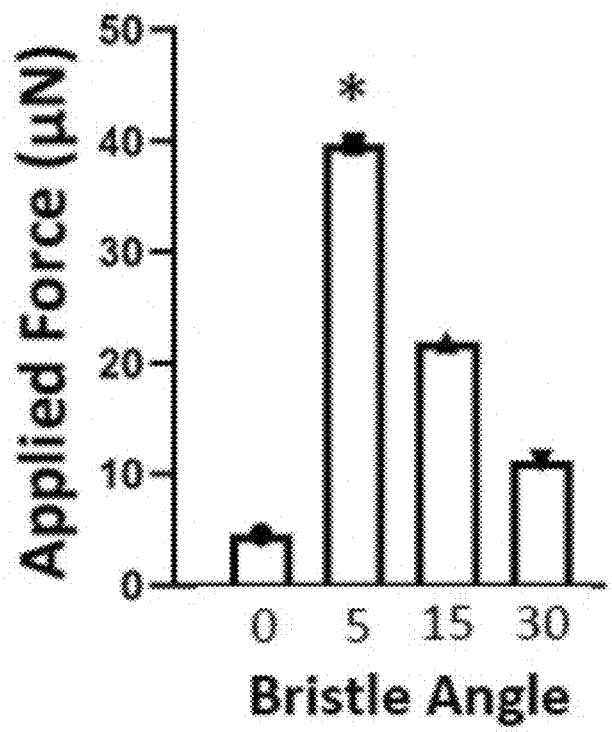
FIG. 16B is a graph of fluent flow simulation applied force at various bristle angles. *p<0.01
Figure 16C:
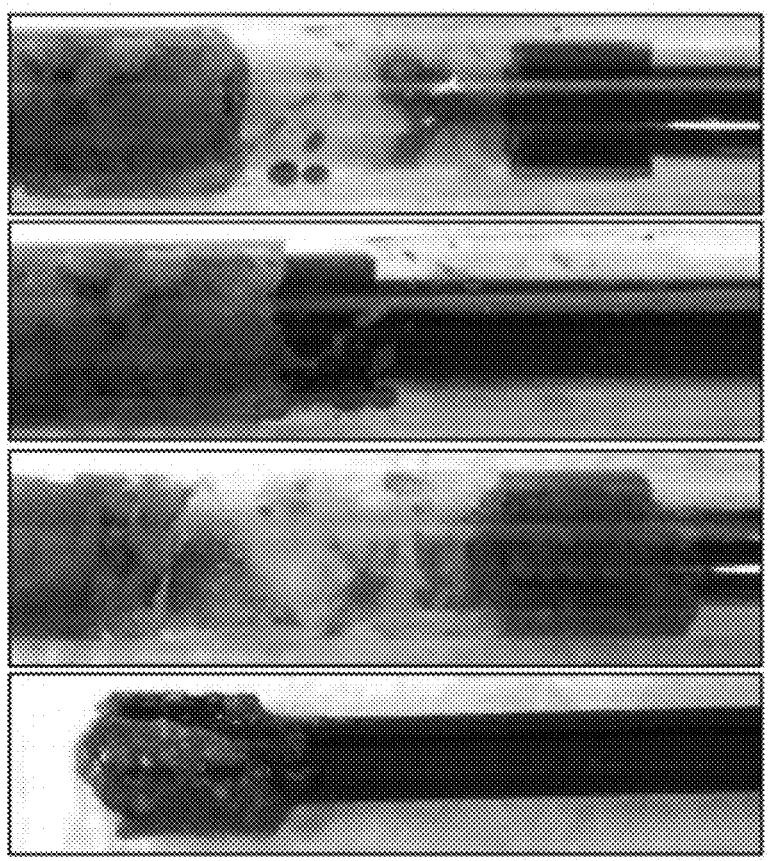
FIG. 16C shows bench-top testing of 5 degree offset agitator that demonstrates drag and retention of clot with a single passage of the agitator into clot.

To test some designs of the agitator and agitator fins, as seen in FIGS. 12A-12F, were varied at 5, 10, 15, and 30 degrees relative to the longitudinal axis of the agitator. Each variation of the agitator was analyzed using a flow simulation with all other variables held constant. The force applied by the forward face of the agitator was determined and used to calculate $C_d$ of each fin angle design. FIG. 16A provides results of the calculated drag coefficient for various fin angle offsets. FIG. 16B provides results of the calculated applied force for various fin angle offsets. In general, drag coefficient and applied force were highest at 5 degrees bristle off-set angle. Bench-top testing of 5 degree offset agitator demonstrated drag and retention of clot with a single passage of the agitator into the clot, as seen in FIG. 16C.

To test some designs of the agitator and agitator fins, as seen in FIGS. 12H and 12I, agitator fin angles were varied at 5, 10, 15, 20, 25, 30, and 90 degrees relative to the central curve of the longitudinal axis. Each variation of the agitator was analyzed using a flow simulation with all other variables held constant. The force F required to hold the agitator in place as a viscous fluid passed across it at a flow rate of v was determined and used to calculate and effective drag coefficient $C_d$ of each fin angle design, where $C_d = 2 F/((v^2) \rho A)$, in which $\rho$ is the fluid density and A is sum of the cross-sectional areas of each agitator and its fins. Table 1 provides results of the calculated drag coefficient for various fin angle offsets, and shows that fin angle acuity affects the drag coefficient.

TABLE 1

| Fin angle (degrees) | Applied Force, F [N] to Hold Hydra Agitator (Averaged Value) | Cross-sectional Area, A [m^2] | Drag Coefficient ($C_d$) |
| --- | --- | --- | --- |
| 90 | 4.57E−06 | 3.12E−05 | 30.1 |
| 5 | 3.98E−05 | 2.68E−05 | 306 |
| 10 | 3.79E−05 | 2.67E−05 | 292 |
| 15 | 2.19E−05 | 2.66E−05 | 169 |
| 20 | 1.24E−05 | 2.64E−05 | 97.0 |
| 25 | 2.46E−05 | 2.63E−05 | 193 |
| 30 | 1.12E−05 | 2.61E−05 | 88.3 |

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

Numerous examples are provided herein to enhance the understanding of the present disclosure. A specific set of statements are provided as follows.

Statement 1: A catheter system for removal of a thrombus from a vessel, comprising: an inner catheter having a proximal end, an infusion segment, and a distal end, the inner catheter comprising: at least one infusion fenestration along the infusion segment; and a distal encapsulation balloon at the distal end; and an outer sheath having a proximal end and a distal end, the outer sheath comprising: a proximal encapsulation balloon at the distal end, wherein the outer sheath surrounds at least a portion of the inner catheter and the distal encapsulation balloon and the proximal encapsulation balloon are separated by a distance along the infusion segment.

Statement 2: The catheter system of Statement 1, wherein the distal encapsulation balloon and the proximal encapsulation balloon are compliant balloons operable to accommodate varying vessel sizes and minimize damage or injury to the vessel.

Statement 3: The catheter system of Statement 1, wherein the distance between the distal encapsulation balloon and the proximal encapsulation balloon is adjustable.

Statement 4: The catheter system of Statement 1, wherein the distance between the distal encapsulation balloon and the proximal encapsulation balloon form a thrombolytic treatment area, wherein the thrombus to be removed is contained within the thrombolytic treatment area.

Statement 5: The catheter system of Statement 4, wherein the infusion segment is within the thrombolytic treatment area.

Statement 6: The catheter system of Statement 5, wherein the inner catheter is operable to infuse a fluid to the thrombolytic treatment area and the outer sheath is operable to provide suction to remove fluid from the thrombolytic treatment area.

Statement 7: The catheter system of Statement 6, wherein the inner catheter and outer sheath are operable to provide isovolumetric suction and restoration of fluid within the thrombolytic treatment area.

Statement 8: The catheter system of Statement 1, wherein the inner catheter further comprises at least three lumina extending from the proximal end to the distal end of the inner catheter.

Statement 9: The catheter system of Statement 8, wherein the inner catheter comprises an inflation lumen, a guide wire lumen, and an infusion lumen, and wherein the at least one infusion fenestration along the infusion segment is connected to the infusion lumen to enable infusion of fluid.

Statement 10: The catheter system of Statement 9, wherein the inner catheter further comprises a manifold at its proximal end comprising an infusion port, a balloon inflation port, and a guidewire access port, wherein each port is fluidly connected to one of the at least three lumina of the inner catheter.

Statement 11: The catheter system of Statement 1, wherein the outer sheath further comprises at least three lumina extending from the proximal end to the distal end of the outer sheath.

Statement 12: The catheter system of Statement 11, wherein the outer sheath comprises an inflation lumen, a suction lumen, and a catheter lumen, and wherein the inner catheter is positioned within the catheter lumen of the outer sheath.

Statement 13: The catheter system of Statement 12, wherein the outer sheath further comprises a manifold at its proximal end comprising a suction port, a balloon inflation port, and a device access port, wherein each port is fluidly connected to one of the at least there lumina of the outer sheath.

Statement 14: The catheter system of Statement 12, wherein the catheter lumen is concentric with the suction lumen.

Statement 15: The catheter system of Statement 1 further comprising an agitator operable to agitate the thrombus.

Statement 16: The catheter system of Statement 15, wherein the outer sheath further encloses the agitator.

Statement 17: The catheter system of Statement 15, wherein the agitator is rail mounted on the outer sheath.

Statement 18: The catheter system of Statement 15, wherein the agitator comprises a plurality of protrusions.

Statement 19: The catheter system of Statement 15, wherein the agitator is configured to protrude from the distal end of the outer sheath.

Statement 20: The catheter system of Statement 15, wherein the agitator is operable to advance and retract over a catheter lumen of the outer sheath.

Statement 21: The catheter system of Statement 15, wherein the agitator is operable to be used without touching a wall of the vessel.

Statement 22: The catheter system of Statement 15, wherein the agitator has a pitch angle operable to reduce shear stress on the vessel during operation of the agitator.

Statement 23: The catheter system of Statement 15, wherein the agitator is brush-like and is operable to clear the thrombus while alleviating radial stresses on the vessel inner wall.

Statement 24: The catheter of claim 15, wherein the protrusions or plurality of protrusions are distributed helically along the length of the agitator.

Statement 25: A catheter for removal of a thrombus from a vessel, comprising: a catheter body having a proximal end and a distal end, the catheter comprising: an encapsulation balloon at the distal end; and an agitator extending from the distal end, beyond the encapsulation balloon.

Statement 26: The catheter of Statement 25, wherein the agitator is operable to not touch a wall of the vessel.

Statement 27: The catheter of Statement 25, wherein the encapsulation balloon is a compliant balloon operable to accommodate varying vessel sizes and minimize damage to the vessel.

Statement 28: A method of removing a thrombus in a patient in need thereof, the method comprising: inserting the catheter system of claim 1 to a treatment area of a vessel; inflating the distal encapsulation balloon through an inflation lumen of the inner catheter; inflating the proximal encapsulation balloon through an inflation lumen of the outer sheath; mechanically lysing the thrombus with an agitator; infusing an infusion solution to the treatment area through the at least one infusion fenestration; applying negative suction to the treatment area through a suction lumen of the outer sheath, wherein there is isovolumetric suction and restoration of fluid within a thrombolytic treatment area between the distal encapsulation balloon and the proximal encapsulation balloon; and removing the catheter system from the patient.

Statement 29: The method of Statement 28, wherein the infusion solution is a thrombolytic solution, saline, or combinations thereof.

Statement 30: The method of Statement 29, wherein the thrombolytic solution comprises tPA.

Statement 31: The method of Statement 28, wherein the negative suction is applied for about 1 to about 30 minutes.

Statement 32: The method of Statement 28, wherein mechanically lysing the thrombus comprises advancing and retracting the agitator over a catheter lumen of the outer sheath.

Statement 33: The method of Statement 28, wherein greater than about 90% luminal patency of the treatment area is restored.

Statement 34: The method of Statement 28, further comprising advancing the catheter system from a femoral vein cannulation or an internal jugular vein cannulation, wherein a pulmonary embolism is treated within the patient.

What is claimed is:

1. A catheter system for removal of a thrombus from a vessel, comprising:
   a multi-lumen inner catheter having a proximal end, an infusion segment, and a distal end, the inner catheter comprising:
   at least one infusion fenestration along the infusion segment; and
   a distal encapsulation balloon at the distal end; and
   a multi-lumen outer sheath having a proximal end and a distal end, the outer sheath comprising:
   at least a catheter lumen and a suction lumen, wherein the catheter lumen is operable to receive the multi-lumen inner catheter; and
   a proximal encapsulation balloon at the distal end; and
   an agitator comprising a longitudinal wall defining an inner lumen operable to receive a longitudinal outer wall of the catheter lumen of the outer sheath such that the agitator is rail-mounted on the catheter lumen and inside the suction lumen when retracted, the agitator operable to agitate or fragment the thrombus,
   wherein inflating the distal encapsulation balloon and the proximal encapsulation balloon encapsulates the thrombus between the balloons, which are separated by an adjustable distance along the infusion segment, thereby forming a thrombolytic treatment area, and wherein when the thrombus is in the thrombolytic treatment area, the catheter system is operable to agitate or fragment the thrombus via the agitator, infuse a fluid through the at least one infusion fenestration, and provide isovolumetric aspiration through the suction lumen.

2. The catheter system of claim 1, wherein the distal encapsulation balloon and the proximal encapsulation balloon are compliant balloons operable to accommodate varying vessel sizes and minimize damage or injury to the vessel.

3. The catheter system of claim 1, wherein the thrombus to be removed is contained within the thrombolytic treatment area.

4. The catheter system of claim 3, wherein the infusion segment is within the thrombolytic treatment area.

5. The catheter system of claim 1, wherein the fluid is a thrombolytic solution, a saline solution, or a combination thereof.

6. The catheter system of claim 1, wherein the at least one infusion fenestration of the inner catheter facilitates fluid administration to the thrombolytic treatment area to prevent venous wall collapse during negative suction from the outer sheath.

7. The catheter system of claim 1, wherein the inner catheter comprises an inflation lumen, a guide wire lumen, and an infusion lumen, and wherein at least one infusion fenestration along the infusion segment is connected to the infusion lumen to enable infusion of the fluid.

8. The catheter system of claim 7, wherein the inner catheter further comprises a manifold at its proximal end comprising an infusion port, a balloon inflation port, and a guidewire access port, wherein each port is fluidly connected to a lumen of the inner catheter.

9. The catheter system of claim 1, wherein the outer sheath further comprises an inflation lumen.

10. The catheter system of claim 9, wherein the outer sheath further comprises a manifold at its proximal end comprising a suction port, a balloon inflation port, and a device access port, wherein each port is fluidly connected to a lumen of the outer sheath.

11. The catheter system of claim 9, wherein the catheter lumen is concentric with the suction lumen.

12. The catheter system of claim 1, wherein the agitator comprises a curved rod or wire.

13. The catheter system of claim 12, wherein the outer sheath encloses the agitator.

14. The catheter system of claim 12, wherein the agitator is configured to protrude from the distal end of the outer sheath, and/or the agitator is operable to advance and retract over a catheter lumen of the outer sheath.

15. The catheter system of claim 12, wherein the agitator is operable to be advanced forward and back and rotated within the thrombolytic treatment area.

16. The catheter system of claim 12, wherein the agitator comprises a plurality of protrusions or brushes at a pitch angle operable to reduce shear stress on the vessel.

17. The catheter system of claim 16, wherein the plurality of protrusions are distributed helically along the length of the agitator.

18. The catheter system of claim 1, wherein the catheter system is sized to remove a large-volume thrombus from a pulmonary artery, vena cava, iliac veins, femoral vein, right atrium, jugular vein, popliteal vein, and/or an ilio-caval venous segment.

19. The catheter system of claim 18, wherein the distal encapsulation balloon has a diameter ranging from 5 mm to 30 mm and the proximal encapsulation balloon has a diameter ranging from 10 mm to 30 mm.

20. The catheter system of claim 1, wherein the thrombolytic treatment area and the infusion segment have a length ranging from 1 cm to 25 cm.

21. The catheter system of claim 20, wherein the inner catheter comprises 1 to 5 fenestrations per cm of the infusion segment.

22. The catheter system of claim 1, wherein the inner catheter comprises a plurality of infusion fenestrations oriented along top, right, and left planes of the infusion segment of the inner catheter.

23. The catheter system of claim 22, wherein the fenestrations are arranged along a centerline of each of the top, right, and left planes, each fenestration separated along its centerline by about 6 mm and each fenestration is separated from its counterpart on an adjacent plane by about 2 mm.

* * * * *

UNITED STATES PATENT AND TRADEMARK OFFICE
CERTIFICATE OF CORRECTION

PATENT NO. : 11,490,910 B2  
APPLICATION NO. : 17/467926  
DATED : November 8, 2022  
INVENTOR(S) : E. Leuthardt et al.

Page 1 of 1

It is certified that error appears in the above-identified patent and that said Letters Patent is hereby corrected as shown below:

In the Specification

Column 1, Line 20 (Governmental Rights): "This invention was made with government support under CMMI1548571 awarded by the National Science Foundation. The government has certain rights in the invention." should read --This work was supported by the U.S. Department of Veterans Affairs, and the Federal Government has certain rights in this invention. This invention was made with government support under CMMI1548571 awarded by the National Science Foundation. The government has certain rights in the invention.--.

Signed and Sealed this  
Second Day of May, 2023

Katherine Kelly Vidal  
*Director of the United States Patent and Trademark Office*